United States Patent
Sekiguchi et al.

(10) Patent No.: US 9,758,765 B2
(45) Date of Patent: Sep. 12, 2017

(54) MODIFIED LAMININ AND USE THEREOF

(75) Inventors: Kiyotoshi Sekiguchi, Osaka (JP);
Yukimasa Taniguchi, Osaka (JP);
Masato Nakagawa, Kyoto (JP)

(73) Assignees: OSAKA UNIVERSITY, Osaka (JP);
KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/110,063

(22) PCT Filed: Apr. 9, 2012

(86) PCT No.: PCT/JP2012/059720
§ 371 (c)(1),
(2), (4) Date: Dec. 24, 2013

(87) PCT Pub. No.: WO2012/137970
PCT Pub. Date: Oct. 11, 2012

(65) Prior Publication Data
US 2014/0127806 A1  May 8, 2014

(30) Foreign Application Priority Data

Apr. 8, 2011  (JP) ................ 2011-086590

(51) Int. Cl.
*C12N 5/074* (2010.01)
*C07K 14/78* (2006.01)

(52) U.S. Cl.
CPC ........... *C12N 5/0696* (2013.01); *C07K 14/78* (2013.01); *C07K 2319/02* (2013.01); *C07K 2319/21* (2013.01); *C07K 2319/42* (2013.01); *C07K 2319/43* (2013.01)

(58) Field of Classification Search
CPC .............................. C12N 5/0696; C07K 14/78
IPC .............................. C12N 5/0696; C07K 14/78
See application file for complete search history.

(56) References Cited

U.S. PATENT DOCUMENTS

2009/0269848 A1  10/2009  Miyazaki et al.

FOREIGN PATENT DOCUMENTS

| EP | 0 704 532 | 4/1996 |
| JP | 5001155 B2 | 8/2012 |
| WO | WO-2008084401 A2 | 7/2008 |
| WO | 2009/123349 | 10/2009 |
| WO | WO-2011043405 A1 | 4/2011 |

OTHER PUBLICATIONS

Desban et al 2006, J. Cell. Sci. 119: 3206-3218.*
Ido et al 2004, J. Biol. Chem. 279: 10946-10954.*
Hozumi et al 2006, J. Biol. Chem. 279: 32929-32940.*
Smirnov et al 2005, J. Biol. Chem. 280: 41449-41457.*
Ogawa et al 2007, Mol. Biol. Cell 18:1621-1633.*
Hozumi et al 2006, J. Biol. Chem. 281:32929-3940.*
McKee et al 2009, J. Biol. Chem. 284:8984-8994.*
Deutzmann et al 1990, Eur. J. Biochem. 191:513-552.*
Miyazaki et al., "Recombinant human laminin isoforms can support the undifferentiated growth of human embryonic stem cells," *Biochemical and Biophysical Research Communications* 375, pp. 27-32 (2008).
Sasaki et al., "Shinkei Soshiki Kochiku no Tameno Kinosei Matrix Tanpakushitsu no Sekkei," *90th Annual Meeting of the Chemical Society of Japan in Spring Koen Yokoshu*, pp. 605, 3 B1-30 (2010).
Rodin et al., "Long-term self-renewal of human pluripotent stem cells on human recombinant laminin-511," *Nature Biotechnology*, vol. 28, No. 6, pp. 611-617 (2010).
Welsh et al., "Engineering the Extracellular Matrix: A Novel Approach to Polymetric Biomaterials. I. Control of the Physical Properties of Artificial Protein Matrices Designed to Support Adhesion of Vascular Endothelial Cells," *Biomacromolecules* 200, vol. 1, pp. 23-30 (2000).
Ido et al., "The Requirement of the Glutamic Acid Residue at the Third Position from the Carboxyl Termini of the Laminin γ Chains in Integrin Binding by Laminins," *Journal of Biological Chemistry*, vol. 282, No. 15, pp. 11144-11154 (2007).
Taniguchi et al., "The C-terminal Region of Laminin β Chains Modulates the Integrin Binding Affinities of Laminins," *J. Biol. Chem.*, vol. 284(12), pp. 7820-7831 (2009).
Manabe et al., "Modulation of Cell-adhesive Activity of Fibronectin by the Alternatively Spliced EDA Segment," *Journal of Cell Biology*, vol. 139, No. 1, pp. 295-307 (1997).
Domogatskaya et al., "Laminin-511 but Not-332,-111, or-411 Enables Mouse Embryonic Stem Cell Self-Renewal In Vitro," *Stem Cells*, vol. 26, pp. 2800-2809 (2008).
International Preliminary Report and Written Opinion in corresponding PCT/JP2012/059720 dated Oct. 8, 2013. English Translation.
International Search Report in corresponding PCT/JP2012/059720 dated Jun. 26, 2012.
Extended European Search Report dated Sep. 10, 2014 issued in corresponding European Patent Application No. 12767444.8.
McKee, K. K. et al., "Scaffold-forming and Adhesive Contributions of Synthetic Laminin-binding Proteins to Basement Membrane Assembly", J. Biol. Chem., Feb. 2, 2009, vol. 284, No. 13, pp. 8984-8994.

(Continued)

*Primary Examiner* — Christopher M Babic
*Assistant Examiner* — Kelaginamane T Hiriyanna
(74) *Attorney, Agent, or Firm* — Wenderoth, Lind & Ponack, L.L.P.

(57) ABSTRACT

Provided are a modified laminin having a cell-growth regulatory molecule bound to at least one site selected from the α chain N-terminus, the α chain C-terminus, the β chain N-terminus and the γ chain N-terminus of laminin or a heterotrimeric laminin fragment, a method for culturing cells in the presence of the modified laminin, a method for establishing iPS cells in the presence of the modified laminin, and a culture substrate coated with the modified laminin. Human stem cells cultured in a xeno-free environment with the use of the modified laminin of the present invention can be provided as highly safe human stem cells applicable to regenerative medicine.

10 Claims, 8 Drawing Sheets

(56) References Cited

OTHER PUBLICATIONS

Nakamura, M. et al., "Construction of a Multi-Functional Extracellular Matrix Protein That Increases Number of N1E-115 Neuroblast Cells Having Neurites", Journal of Biomedical Materials Research; Jun. 1, 2009, vol. 91B, No. 1, pp. 425-426.
Hiraoka, M. et al., "Enhanced Survival of Neural Cells Embedded in Hydrogels Composed of Collagen and Laminin-Derived Cell Adhesive Peptide", Bioconjugate Chemistry, Apr. 7, 2009, vol. 20, No. 5, pp. 976-983.
Prowse, A. B. J., et al., "Stem cell integrins: Implications for ex-vivo culture and cellular therapies", Stem Cell Research, Jan. 1, 2011, vol. 6, No. 1, pp. 1-12.
Nakagawa, M. et al., "A novel efficient feeder-free culture system for the derivation of human induced pluripotent stem cells", Scientific Reports, Jan. 8, 2014, vol. 4, pp. 1-7.
Miyazaki, T. et al., "Laminin E8 fragments support efficient adhesion and expansion of dissociated human pluripotent stem cells", Nature Communications, Dec. 4, 2012, vol. 3, p. 1236.
Kikkawa et al., "Mesangial cells organize the glomerular capillaries by adhering to the G domain of laminin alpha5 in the glomerular basement membrane", The Journal of Cell Biology, 2003, vol. 161, No. 1, pp. 187-196.
Kammerer et al., "Interaction of agrin with laminin requires a coiled-coil conformation of the agrin-binding site within the laminin [gamma] 1 chain", The EMBO Journal, 1999, vol. 18, No. 23, pp. 6762-6770.
Smirnov et al., "Contributions of the LG Modules and Furin Processing to Laminin-2 Functions", The Journal of Biological Chemistry, 2002, vol. 277, No. 21, pp. 18928-18937.

\* cited by examiner

[Fig. 1]
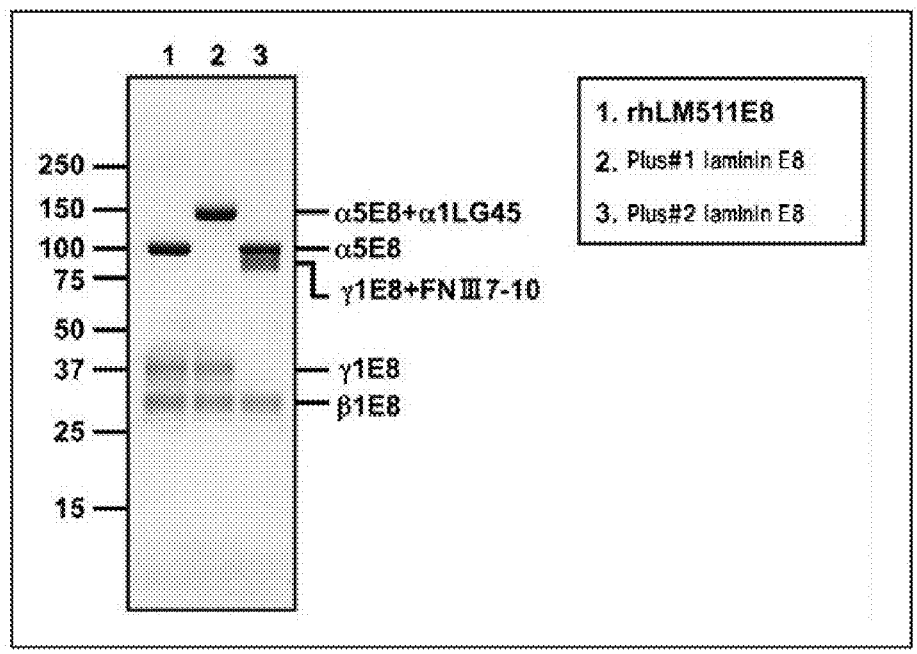
[Fig. 2]
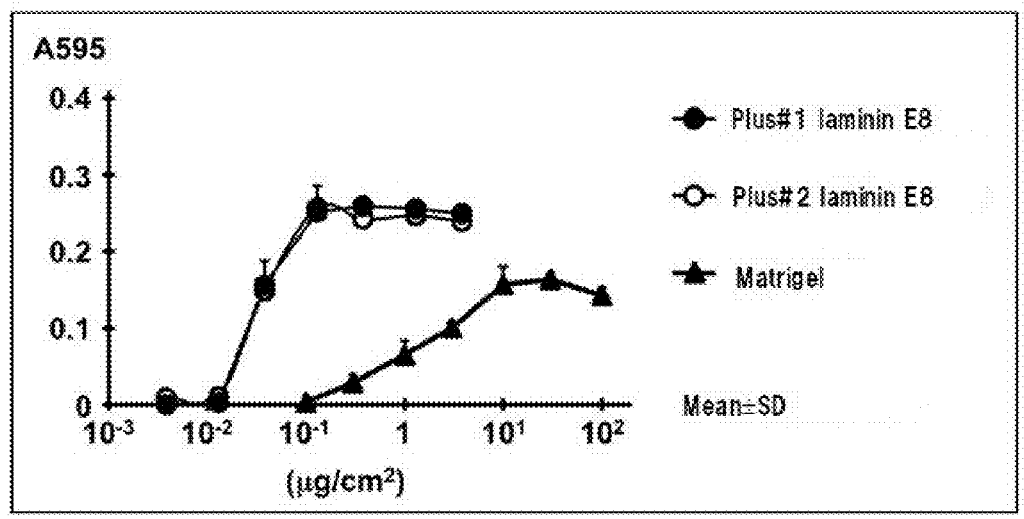

[Fig. 3]
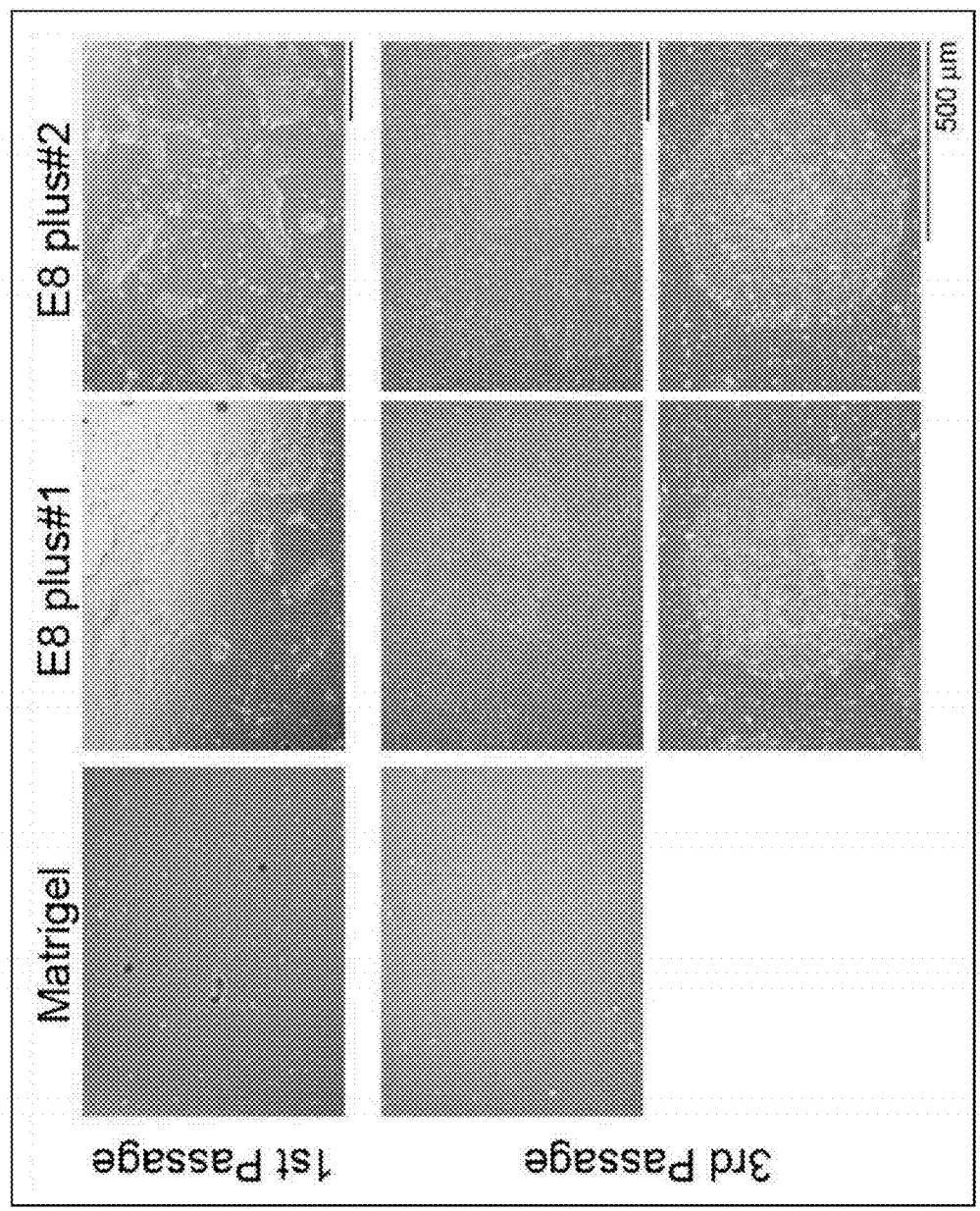

[Fig. 4]
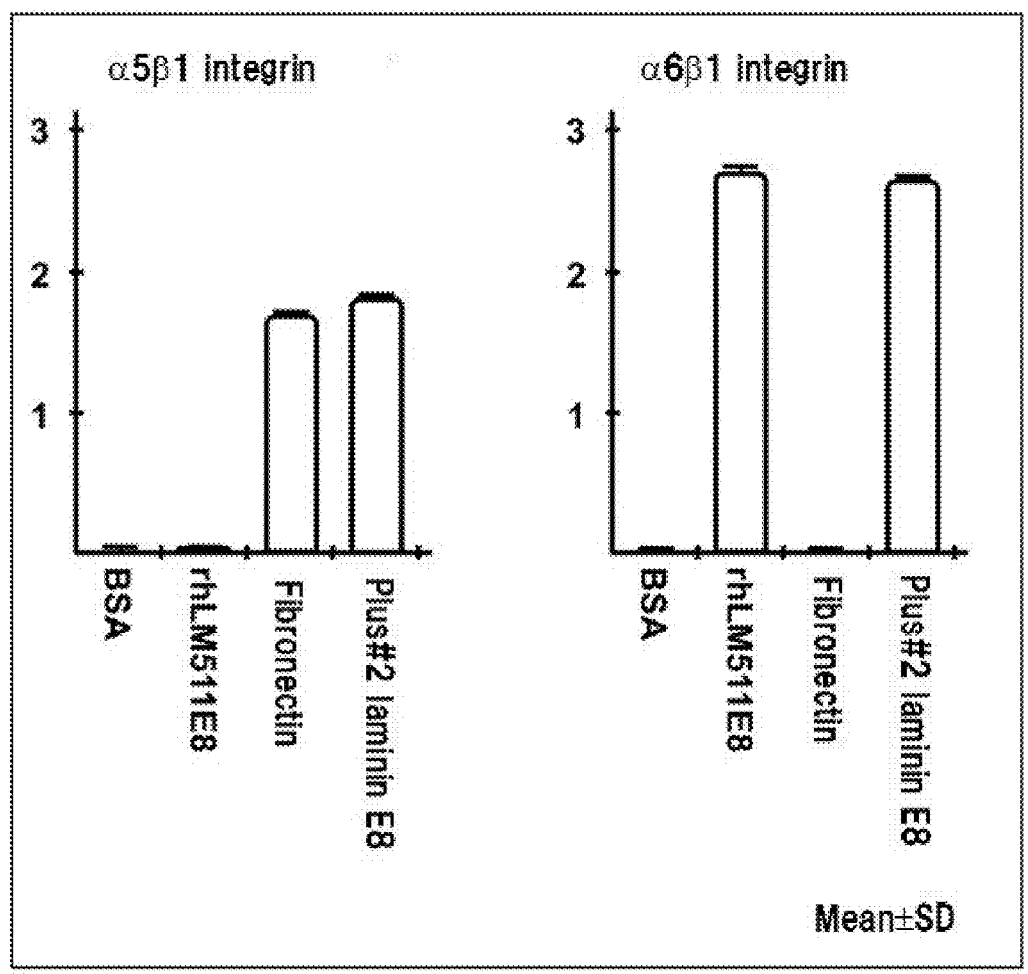

[Fig. 5]
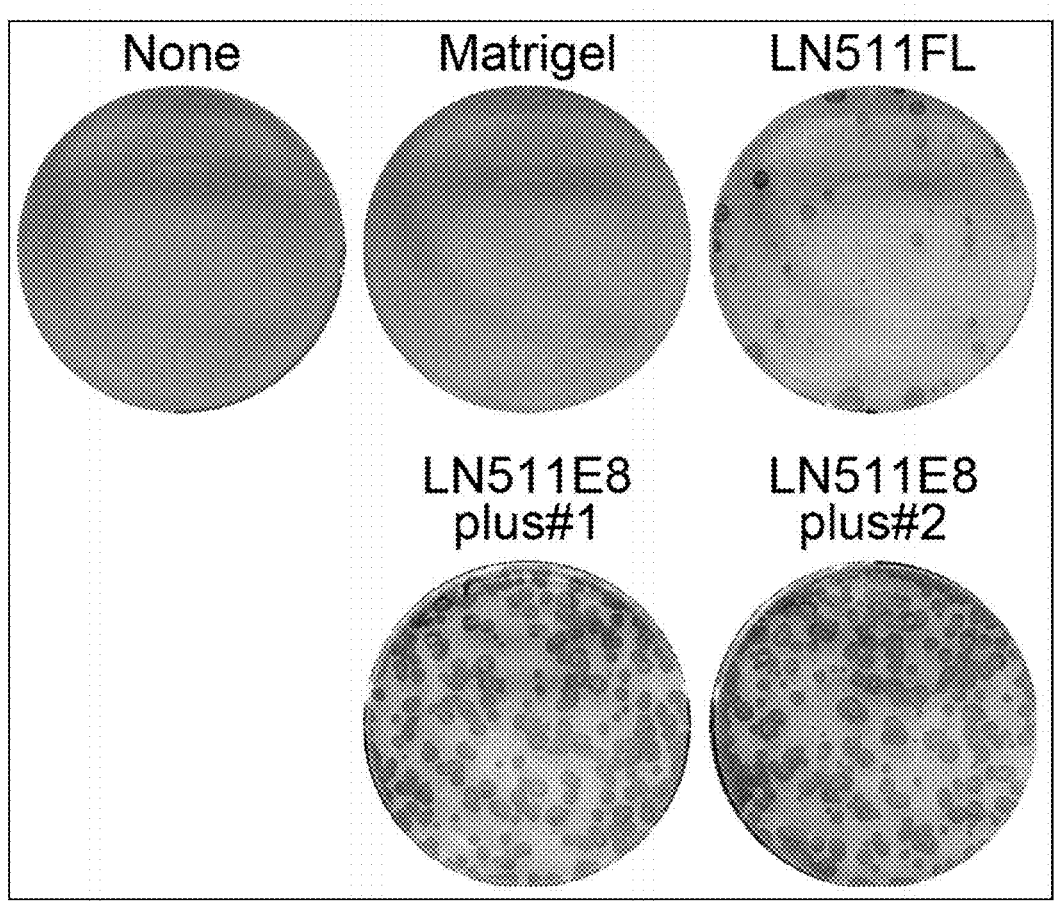

[Fig. 6]
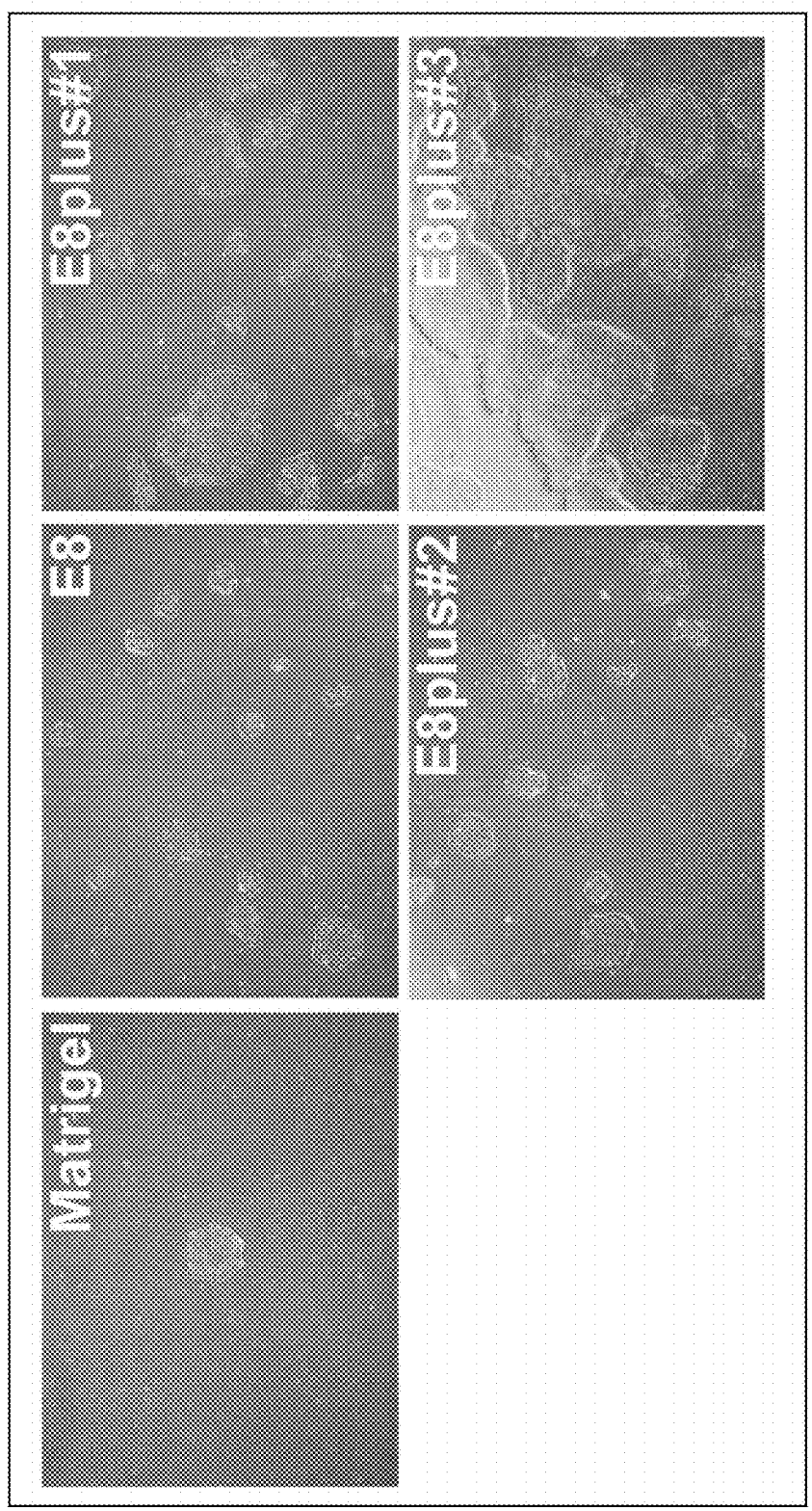

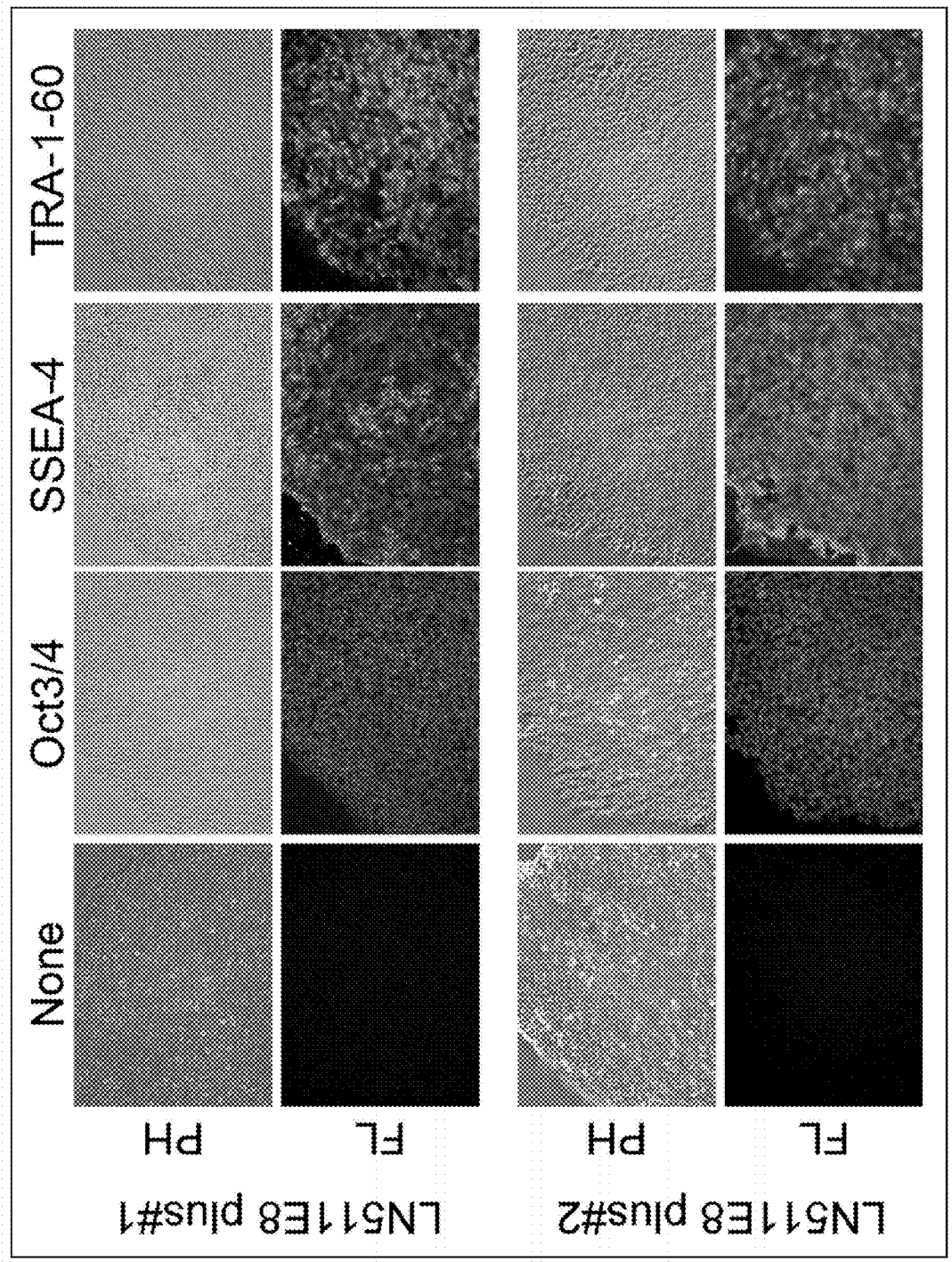
[Fig. 7]

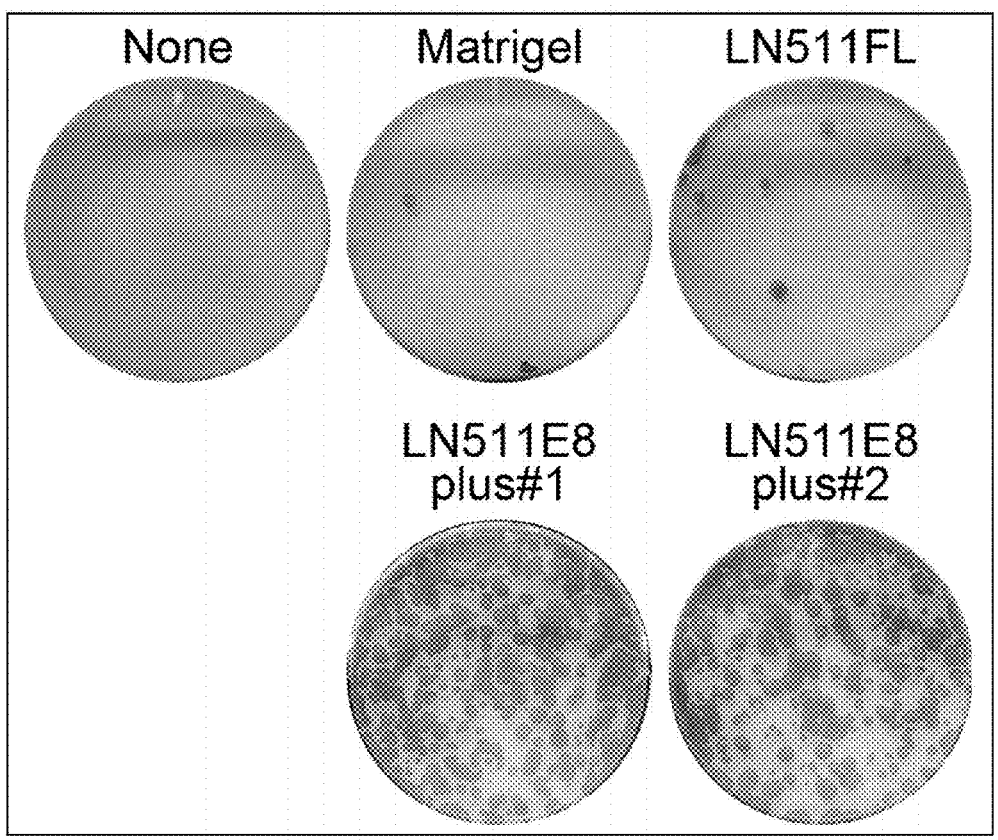
[Fig. 8]

[Fig. 9]
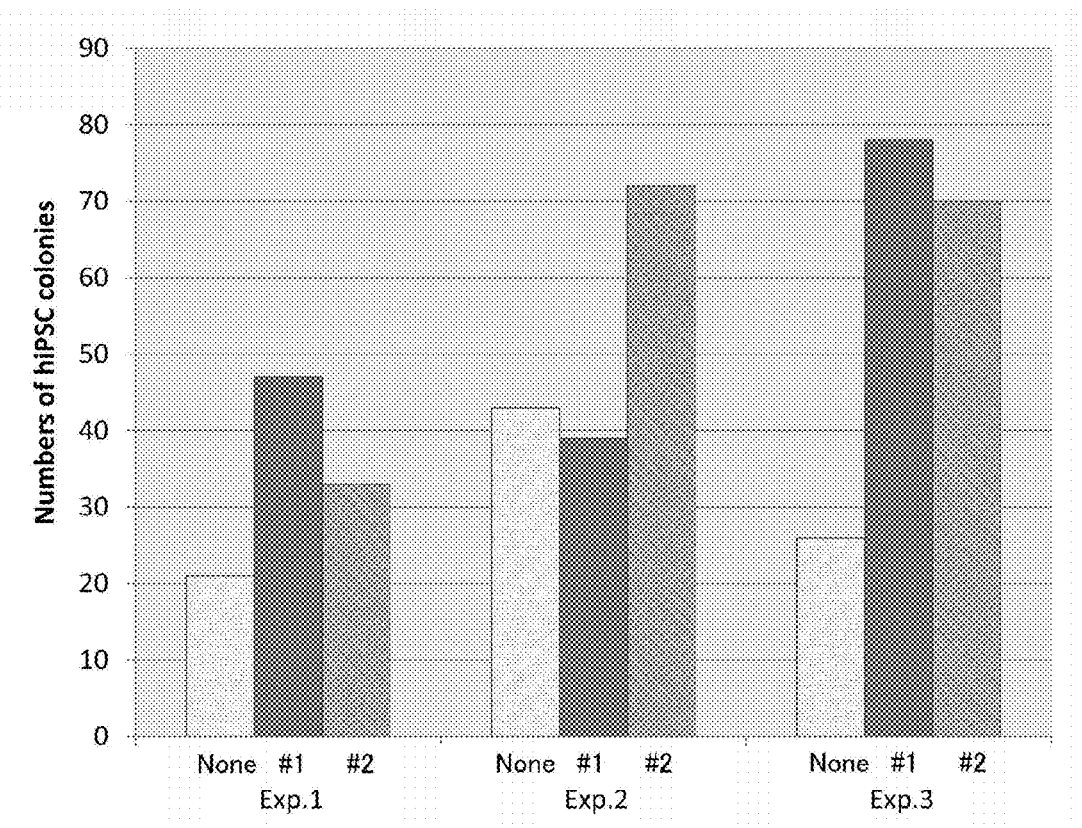
[Fig. 10]
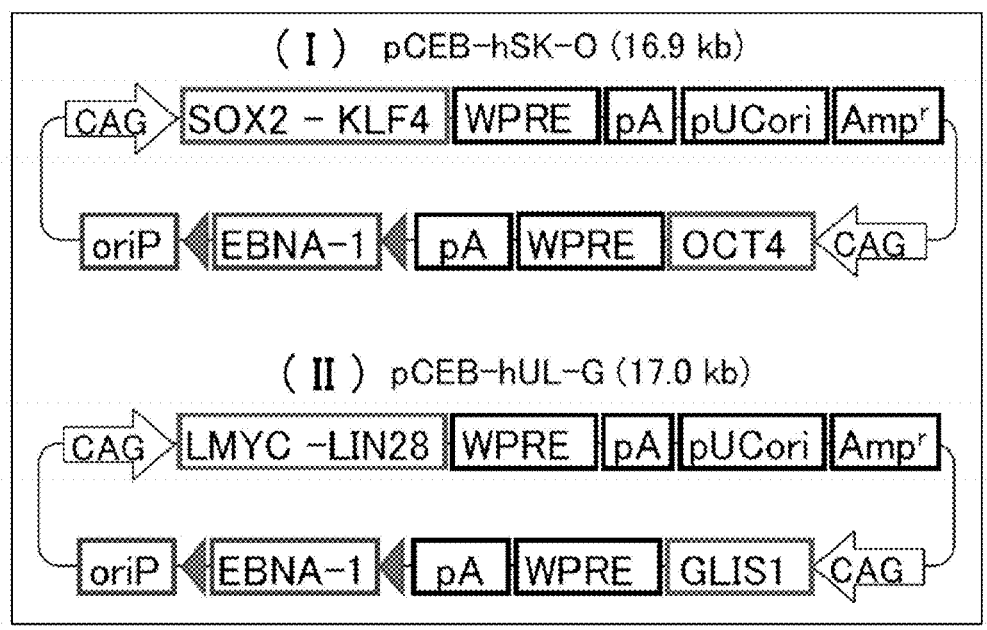

SEQUENCE LISTING

<160> NUMBER OF SEQ ID NOS: 24

<210> SEQ ID NO 1
<211> LENGTH: 26
<212> TYPE: DNA
<213> ORGANISM: Artificial Sequence
<220> FEATURE:
<223> OTHER INFORMATION: Primer Sequence

<400> SEQUENCE: 1
atgatgatga agcttatcga taccgt                                        26

<210> SEQ ID NO 2
<211> LENGTH: 26
<212> TYPE: DNA
<213> ORGANISM: Artificial Sequence
<220> FEATURE:
<223> OTHER INFORMATION: Primer Sequence

<400> SEQUENCE: 2

-continued

```
catcatcatg atatcgaatt cctgca                                          26

<210> SEQ ID NO 3
<211> LENGTH: 29
<212> TYPE: DNA
<213> ORGANISM: Artificial Sequence
<220> FEATURE:
<223> OTHER INFORMATION: Primer Sequence

<400> SEQUENCE: 3
atcatatgga taaagcttat cgataccgt                                       29

<210> SEQ ID NO 4
<211> LENGTH: 29
<212> TYPE: DNA
<213> ORGANISM: Artificial Sequence
<220> FEATURE:
<223> OTHER INFORMATION: Primer Sequence

<400> SEQUENCE: 4
gtgccagatt atgcagatat cgaattcct                                       29

<210> SEQ ID NO 5
<211> LENGTH: 29
<212> TYPE: DNA
<213> ORGANISM: Artificial Sequence
<220> FEATURE:
<223> OTHER INFORMATION: Primer Sequence

<400> SEQUENCE: 5
atccttgtaa tcaagcttat cgataccgt                                       29

<210> SEQ ID NO 6
<211> LENGTH: 26
<212> TYPE: DNA
<213> ORGANISM: Artificial Sequence
<220> FEATURE:
<223> OTHER INFORMATION: Primer Sequence

<400> SEQUENCE: 6
gatgatgata aggatatcga attcct                                          26

<210> SEQ ID NO 7
<211> LENGTH: 25
<212> TYPE: DNA
<213> ORGANISM: Artificial Sequence
<220> FEATURE:
<223> OTHER INFORMATION: Primer Sequence

<400> SEQUENCE: 7
gctgccgagg atgctgctgg ccagg                                           25

<210> SEQ ID NO 8
<211> LENGTH: 25
<212> TYPE: DNA
<213> ORGANISM: Artificial Sequence
<220> FEATURE:
<223> OTHER INFORMATION: Primer Sequence

<400> SEQUENCE: 8
ctaggcagga tgccgggcgg gctga                                           25

<210> SEQ ID NO 9
<211> LENGTH: 25
<212> TYPE: DNA
<213> ORGANISM: Artificial Sequence
```

```
<220> FEATURE:
<223> OTHER INFORMATION: Primer Sequence

<400> SEQUENCE: 9
cttcagcata gtgctgctga cattg                                  25

<210> SEQ ID NO 10
<211> LENGTH: 27
<212> TYPE: DNA
<213> ORGANISM: Artificial Sequence
<220> FEATURE:
<223> OTHER INFORMATION: Primer Sequence

<400> SEQUENCE: 10
ttacaagcat gtgctataca cagcaac                                27

<210> SEQ ID NO 11
<211> LENGTH: 25
<212> TYPE: DNA
<213> ORGANISM: Artificial Sequence
<220> FEATURE:
<223> OTHER INFORMATION: Primer Sequence

<400> SEQUENCE: 11
aatgacattc tcaacaacct gaaag                                  25

<210> SEQ ID NO 12
<211> LENGTH: 25
<212> TYPE: DNA
<213> ORGANISM: Artificial Sequence
<220> FEATURE:
<223> OTHER INFORMATION: Primer Sequence

<400> SEQUENCE: 12
ctagggcttt tcaatggacg gggtg                                  25

<210> SEQ ID NO 13
<211> LENGTH: 34
<212> TYPE: DNA
<213> ORGANISM: Artificial Sequence
<220> FEATURE:
<223> OTHER INFORMATION: Primer Sequence

<400> SEQUENCE: 13
caatgatctg gagctggccg acgcctacta cctg                        34

<210> SEQ ID NO 14
<211> LENGTH: 28
<212> TYPE: DNA
<213> ORGANISM: Artificial Sequence
<220> FEATURE:
<223> OTHER INFORMATION: Primer Sequence

<400> SEQUENCE: 14
ctctgcatca ggccccaggc ccggggtc                               28

<210> SEQ ID NO 15
<211> LENGTH: 27
<212> TYPE: DNA
<213> ORGANISM: Artificial Sequence
<220> FEATURE:
<223> OTHER INFORMATION: Primer Sequence

<400> SEQUENCE: 15
cctggggcct gatgcagagg acagcaa                                27
```

<210> SEQ ID NO 16
<211> LENGTH: 35
<212> TYPE: DNA
<213> ORGANISM: Artificial Sequence
<220> FEATURE:
<223> OTHER INFORMATION: Primer Sequence

<400> SEQUENCE: 16
aaactcagga ctcggtccca ggacaggaat gaagg      35

<210> SEQ ID NO 17
<211> LENGTH: 34
<212> TYPE: DNA
<213> ORGANISM: Artificial Sequence
<220> FEATURE:
<223> OTHER INFORMATION: Primer Sequence

<400> SEQUENCE: 17
gaggtctata taagcagagc tctctggcta acta       34

<210> SEQ ID NO 18
<211> LENGTH: 34
<212> TYPE: DNA
<213> ORGANISM: Artificial Sequence
<220> FEATURE:
<223> OTHER INFORMATION: Primer Sequence

<400> SEQUENCE: 18
tggtggagac aatggatcct tatcatcatc atcc       34

<210> SEQ ID NO 19
<211> LENGTH: 35
<212> TYPE: DNA
<213> ORGANISM: Artificial Sequence
<220> FEATURE:
<223> OTHER INFORMATION: Primer Sequence

<400> SEQUENCE: 19
taattaccga acagataatg acattctcaa caacc      35

<210> SEQ ID NO 20
<211> LENGTH: 23
<212> TYPE: DNA
<213> ORGANISM: Artificial Sequence
<220> FEATURE:
<223> OTHER INFORMATION: Primer Sequence

<400> SEQUENCE: 20
gaaaggacag tgggagtggc acc                   23

<210> SEQ ID NO 21
<211> LENGTH: 34
<212> TYPE: DNA
<213> ORGANISM: Artificial Sequence
<220> FEATURE:
<223> OTHER INFORMATION: Primer Sequence

<400> SEQUENCE: 21
gatgatgata aggatccatt gtctccacca acaa       34

<210> SEQ ID NO 22
<211> LENGTH: 35
<212> TYPE: DNA
<213> ORGANISM: Artificial Sequence
<220> FEATURE:
<223> OTHER INFORMATION: Primer Sequence

```
-continued

<400> SEQUENCE: 22
atgtcattat ctgttcggta attaatggaa attgg                              35

<210> SEQ ID NO 23
<211> LENGTH: 30
<212> TYPE: DNA
<213> ORGANISM: Artificial Sequence
<220> FEATURE:
<223> OTHER INFORMATION: Primer Sequence

<400> SEQUENCE: 23
acgaagcttg ggctgagggc atacgatggc                                    30

<210> SEQ ID NO 24
<211> LENGTH: 31
<212> TYPE: DNA
<213> ORGANISM: Artificial Sequence
<220> FEATURE:
<223> OTHER INFORMATION: Primer Sequence

<400> SEQUENCE: 24
ataaagcttc tcgaccacca gtggggcttg g                                  31
```

MODIFIED LAMININ AND USE THEREOF

TECHNICAL FIELD

The present invention relates to a modified human laminin and use thereof. In particular, the present invention relates to a modified human laminin having a cell-growth regulatory molecule bound to laminin or a fragment thereof, a method for culturing cells using the modified human laminin, a method for establishing iPS cells using the modified human laminin, and a culture substrate coated with the modified human laminin.

BACKGROUND ART

Stem cells, in particular pluripotent stem cells such as ES cells and iPS cells, are receiving worldwide attention for their potential application to regenerative medicine. The culture and maintenance of stem cells without loss of their pluripotency usually requires the presence of feeder cells in the culture system, and as such feeder cells, mouse embryonic fibroblasts (MEFs) whose division has been arrested by radiation or antibiotic treatment are used. As the MEFs, STO cells etc. are usually often used, and SNL cells (McMahon, A. P. & Bradley, A. Cell 62, 1073-1085 (1990)) etc. are often used for generation of iPS cells. However, the use of feeder cells is a great restriction on clinical application of stem cells. In order to solve this problem, various cell adhesion molecules in place of feeder cells have been tried out as an extracellular matrix for stem cells. Among these, crude extracts prepared from mouse EHS sarcoma known to excessively produce basement membrane components (commercially available under the trade name of Matrigel) are reportedly highly effective for maintenance of the pluripotency of stem cells. Matrigel is known to abundantly contain basement membrane components such as laminin and type IV collagen, but the complete composition of Matrigel is still unknown. Further, Matrigel is a mouse derived product, and thus is not suitable for human stem cell culture in regenerative medicine.

For application of human stem cells to regenerative medicine, a feeder-free (no feeder cells are used) and xeno-free (the culture system contains no xenogeneic components) culture environment is desirable. Therefore, as an extracellular matrix of human origin, human vitronectin and human fibronectin have been tried out, but as compared with Matrigel, they are neither superior in maintenance of undifferentiated state of human stem cells or in adhesion efficiency thereof, nor satisfactory in terms of quality, source material availability, safety, etc. Thus, there is much to be improved in the development of extracellular matrices suitable for maintenance culture of human stem cells to be applied to regenerative medicine, and the development of new human-stem-cell culture techniques using human extracellular matrices having a uniform chemical composition is strongly desired.

Laminin is a major cell-adhesion molecule present in the basement membrane. Laminin is a large heterotrimeric glycoprotein consisting of three subunits termed $\alpha$, $\beta$ and $\gamma$ chains, and has a molecular weight of 800,000 Da. The three subunits associate with each other through their coiled-coil domains in the C-terminal regions and assemble into a heterotrimer that is stabilized by disulfide bonds therein. The present inventors reported that recombinant human laminins (particularly, laminin 332, which consists of $\alpha 3$, $\beta 3$ and $\gamma 2$ chains, and laminin 511, which consists of $\alpha 65$, $\beta 1$ and $\gamma 1$ chains) are effective for maintaining the pluripotency of human ES cells (see Non Patent Literature 1). However, on the surfaces of human stem cells, adhesion receptors (membrane-bound molecules that are found on cell surfaces and mediate cell adhesion to extracellular matrices) other than laminin receptors are also expressed, and laminin molecules alone cannot use these adhesion receptors effectively. Then, strongly desired is the development of novel human extracellular matrices that have as natural an adhesion activity as possible and enable human stem cell culture in feeder-free conditions.

CITATION LIST

Non Patent Literature

Non Patent Literature 1:
Miyazaki T, Futaki S, Hasegawa K, Kawasaki M, Sanzen N, Hayashi M, Kawase E, Sekiguchi K, Nakatsuji N, Suemori H. Recombinant human laminin isoforms can support the undifferentiated growth of human embryonic stem cells. Biochem. Biophys. Res. Commun. 375: 27-35, 2008.

SUMMARY OF INVENTION

Technical Problem

An object of the present invention is to provide a culture substrate which enables maintenance culture of stem cells while supporting their pluripotency in a feeder-free environment, a method for culturing cells using the culture substrate, a method for establishing iPS cells using the culture substrate, and a culture substrate coated with a certain extracellular matrix.

Solution to Problem

The present invention includes the following as a solution to the above-mentioned problems.
[1] A modified laminin having a cell-growth regulatory molecule bound to at least one site selected from the $\alpha$ chain N-terminus, the $\alpha$ chain C-terminus, the $\beta$ chain N-terminus and the $\gamma$ chain N-terminus of laminin or a heterotrimeric laminin fragment.
[2] The modified laminin according to the above [1], wherein the cell-growth regulatory molecule is a cell adhesion molecule.
[3] The modified laminin according to the above [1], wherein the cell-growth regulatory molecule is a growth factor binding molecule.
[4] The modified laminin according to any one of the above [1] to [3], wherein the laminin fragment has integrin binding activity.
[5] The modified laminin according to the above [4], wherein the laminin fragment is a laminin E8 fragment.
[6] The modified laminin according to any one of the above [1] to [5], wherein the laminin consists of one kind of $\alpha$ chain selected from $\alpha 1$ to $\alpha 5$, one kind of $\beta$ chain selected from $\beta 1$ to $\beta 3$, and one kind of $\gamma$ chain selected from $\gamma 1$ to $\gamma 3$.
[7] The modified laminin according to the above [6], wherein the laminin is laminin $\alpha 5\beta 1\gamma 1$ or laminin $\alpha 3\beta 3\gamma 2$.
[8] The modified human laminin according to the above [2], wherein the cell adhesion molecule is one or more kinds selected from
(a) cell adhesion molecules capable of binding to integrins,
(b) cell adhesion molecules capable of binding to membrane-bound proteoglycans, (c) cell adhesion molecules capable of binding to discoidin domain receptors,
(d) cell adhesion molecules capable of binding to dystroglycans, and
(e) cell adhesion molecules capable of binding to cell surface sugar chains.

[9] The modified human laminin according to the above [2], wherein the cell adhesion molecule is one or more kinds selected from
(a) fibronectin or a fragment having a cell adhesion domain thereof,
(b) collagen or a fragment having a cell adhesion domain thereof,
(c) vitronectin or a fragment having a cell adhesion domain thereof,
(d) nephronectin or a fragment having a cell adhesion domain thereof,
(e) osteopontin or a fragment having a cell adhesion domain thereof,
(f) MAEG or a fragment having a cell adhesion domain thereof,
(g) tenascin or a fragment having a cell adhesion domain thereof,
(h) SVEP1 or a fragment having a cell adhesion domain thereof,
(i) TGF-β1 latency associated peptide or a fragment having a cell adhesion domain thereof,
(j) TGF-β3 latency associated peptide or a fragment having a cell adhesion domain thereof, and
(k) globular domains 4 and/or 5 of a laminin α chain.

[10] The modified human laminin according to the above [3], wherein the growth factor binding molecule is one or more kinds selected from
(a) perlecan or a fragment having a growth factor binding domain thereof,
(b) agrin or a fragment having a growth factor binding domain thereof,
(c) XVIII type collagen or a fragment having a growth factor binding domain thereof,
(d) syndecan or a fragment having a growth factor binding domain thereof,
(e) glypican or a fragment having a growth factor binding domain thereof, and
(f) latent TGF-β binding protein or a fragment having a growth factor binding domain thereof.

[11] The modified laminin according to any one of the above [1] to [10], which is of human origin.

[12] A method for culturing mammalian cells, characterized by culturing the cells in the presence of the modified human laminin according to any one of the above [1] to [11].

[13] The method according to the above [12], wherein the mammalian cells are ES cells, iPS cells or somatic stem cells.

[14] The method according to the above [12] or [13], wherein no feeder cells are used.

[15] A culture substrate coated with the modified human laminin according to any one of the above [1] to [11].

[16] The culture substrate according to the above [15], wherein the coating concentration of the modified human laminin is 0.03 to 25 μg/cm².

[17] A method for establishing iPS cells, comprising the step of bringing a nuclear reprogramming substance into contact with somatic cells in the presence of the modified human laminin according to any one of the above [1] to [11].

[18] The method according to the above [17], wherein the nuclear reprogramming substance comprises one or more kinds of substances selected from the group consisting of Oct family members, Sox family members, Klf family members, Lin family members, Glis family members, and nucleic acids encoding the foregoing.

Advantageous Effects of Invention

According to the present invention, a modified human laminin used as an extracellular matrix which enables maintenance culture of stem cells while supporting their pluripotency in a feeder-free environment, a method for culturing cells using the modified human laminin, a method for establishing iPS cells using the modified human laminin, and a culture substrate coated with the modified human laminin can be provided. Through establishment of iPS cells or culture of human stem cells in a xeno-free culture medium with the use of the modified human laminin, highly safe human stem cells applicable to regenerative medicine can be provided.

BRIEF DESCRIPTION OF DRAWINGS

FIG. 1 shows the results of SDS-PAGE analysis of a modified human laminin in which the 4th and 5th globular domains of the human laminin α1 chain are fused with the E8 fragment of recombinant human laminin α5β1γ1 (hereinafter referred to as "Plus#1 laminin E8") and a modified human laminin in which the cell adhesion domain of human fibronectin is fused with the E8 fragment of human laminin α5β1γ1 (hereinafter referred to as "Plus#2 laminin E8").

FIG. 2 shows the comparison of the coating concentration-dependent adhesion efficiencies of human iPS cells on Plus#1 laminin E8, Plus#2 laminin E8 and Matrigel.

FIG. 3 shows the images of the human iPS cells at the 1st and 3rd passage generation on the culture substrate coated with Plus#1 laminin E8, Plus#2 laminin E8 or Matrigel.

FIG. 4 shows the binding activities of Plus#2 laminin E8 for recombinant human α5β1 integrin and recombinant human α6β1 integrin.

FIG. 5 shows the images of the human ES cells in single-cell culture using the culture substrate coated with Plus#1 laminin E8, Plus#2 laminin E8, full-length laminin 511 or Matrigel.

FIG. 6 shows the images of the human iPS cells that are alive and attached after 7-day culture using the culture substrate coated with Plus#1 laminin E8, Plus#2 laminin E8, a modified human laminin in which the domains I to III of human perlecan are fused with the E8 fragment of human laminin α5β1γ1 (hereinafter referred to as "Plus#3 laminin E8"), the E8 fragment of human laminin α5β1γ1 or Matrigel.

FIG. 7 shows the results of the immunostaining for undifferentiation markers Oct3/4, SSEA-4 and TRA-1-60 in the human iPS cells passaged to the 10th generation on the culture substrate coated with Plus#1 laminin E8 or Plus#2 laminin E8.

FIG. 8 shows the images of the human iPS cells in single-cell culture using the culture substrate coated with Plus#1 laminin E8, Plus#2 laminin E8, full-length laminin 511 or Matrigel.

FIG. 9 shows the results of the attempt to establish human iPS cells from human adult dermal fibroblasts using the non-coated dish, the Plus#1 laminin E8-coated dish and the Plus#2 laminin E8-coated dish.

FIG. 10 shows the structures of episomal plasmid vectors pCEB-hSK-O (shown in (I)) and pCEB-hUL-G (shown in (II)).

DESCRIPTION OF EMBODIMENTS

<Modified Human Laminin>

The present invention provides a modified laminin having a cell-growth regulatory molecule bound to at least one site selected from the α chain N-terminus, the α chain C-terminus, the β chain N-terminus and the γ chain N-terminus of laminin or a heterotrimeric laminin fragment.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms (see Table 1). The laminin which constitutes the modified laminin of the present invention may be any of these isoforms. That is, the laminin which constitutes the modified laminin of the present invention consists of one kind of α chain selected from α1 to α5, one kind of β chain selected from β1 to β3, and one kind of γ chain selected from γ1 to γ3. Specifically, the 12 kinds of isoforms shown in Table 1 and all the other possible isoforms can preferably be used. Preferred is laminin α3β3γ2 or laminin α5β1γ1.

TABLE 1

| α chain | Trimer composition |
|---|---|
| α1 | α1β1γ1 (laminin-1) |
|  | α1β2γ1 (laminin-3) |
| α2 | α2β1γ1 (laminin-2) |
|  | α2β2γ1 (laminin-4) |
|  | α2β1γ3 (laminin-12) |
| α3 | α3β3γ2 (laminin-5) |
|  | α3β1γ1 (laminin-6) |
|  | α3β2γ1 (laminin-7) |
| α4 | α4β1γ1 (laminin-8) |
|  | α4β2γ1 (laminin-9) |
| α5 | α5β1γ1 (laminin-10) |
|  | α5β2γ1 (laminin-11) |

The origin of the laminin is not particularly limited and laminins derived from various organisms can be used. Preferred are laminins derived from mammals including but not limited to humans, mice, rats, cattle and pigs. Among these, human laminins are particularly preferably used. In the case where human stem cells are cultured for preparation of materials for human regenerative medicine, a xeno-free (the culture system contains no xenogeneic components) environment is required, and for this reason, human laminins are preferably used.

The laminin which constitutes the modified laminin of the present invention may be a full-length laminin or a fragment thereof. That is, the laminin may be a full-length laminin consisting of a full-length α chain, a full-length β chain and a full-length γ chain, or a laminin fragment consisting of α, β and γ chains among which one or more chains are fragments shorter than the corresponding full-length chains. The laminin fragment need to be in the form of a heterotrimer, and preferably has integrin binding activity. The heterotrimer formation of the laminin fragment can be confirmed from, for example, the number of bands detected by SDS-PAGE (see Example 1). The integrin binding activity of the laminin fragment can be confirmed by ELISA etc. (see Example 4).

The laminin fragment which constitutes the modified laminin of the present invention need to be in the form of a heterotrimer consisting of α, β and γ chains, but the molecular weight etc. of the laminin fragment are not particularly limited. In terms of the strength of integrin binding activity and the efficiency of recombinant protein expression (higher yield can be obtained as compared with a full-length laminin), a laminin E8 fragment is preferred. The laminin E8 fragment was identified as a fragment having the strongest cell adhesion activity among fragments obtained by elastase digestion of mouse laminin α1β1γ1 (hereinafter referred to as "mouse laminin 111") (Edgar D., Timpl R., Thoenen H. The heparin-binding domain of laminin is responsible for its effects on neurite outgrowth and neuronal survival. EMBO J., 3: 1463-1468, 1984; and Goodman S L., Deutzmann R., von der Mark K. Two distinct cell-binding domains in laminin can independently promote nonneuronal cell adhesion and spreading. J. Cell Biol., 105: 589-598, 1987). It is presumed that elastase digestion of laminins other than mouse laminin 111 could produce fragments corresponding to the mouse laminin 111 E8 fragment, but there is no reports on isolation or identification of such fragments. Therefore, the laminin E8 used in the present invention does not have to be an elastase-digested product of laminin, and may be any laminin fragment having the cell adhesion activity, structure and molecular weight equivalent to those of mouse laminin 111E8.

The laminin may be a native laminin or a mutant laminin that has modification(s) of one or more amino acid residues but retains biological activities of the native laminin. The method for producing the laminin is not particularly limited. For example, the laminin can be obtained by purification from highly laminin-expressing cells. Alternatively, the laminin can be produced as a recombinant protein. The method for producing the laminin fragment is not particularly limited, either. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin and the laminin fragment are produced as a recombinant protein.

The recombinant laminin and the recombinant laminin fragment can be produced by appropriate known recombinant techniques, for example, by preparing DNAs encoding full-length or partial-length laminin α, β and γ chains, inserting the DNAs into separate expression vectors, co-introducing the three resulting expression vectors into appropriate host cells, and purifying the expressed trimeric protein by a known method. Examples of the method for producing the recombinant laminin (full-length laminin) include, but are not limited to, the method of Ido et al. (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004). Examples of the method for producing of the recombinant laminin fragment (human laminin E8) include, but are not limited to, the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

The nucleotide and amino acid sequence data of the genes encoding α, β and γ chains which constitute laminins derived from major mammals can be obtained from known databases (GenBank etc.). The accession numbers of the constituent chains of laminins derived major mammals including humans are shown in Table 1. The nucleotide and amino acid sequence data of the constituent chains of laminins derived from other mammals can also be obtained from known databases (GenBank etc.).

TABLE 2

|  | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |
| Mouse laminin α5 chain | NP_001074640 | NM_001081171 |
| Mouse laminin β1 chain | NP_032508 | NM_008482 |
| Mouse laminin γ1 chain | NP_034813 | NM_010683 |
| Rat laminin α5 chain | NP_001178538 | NM_001191609 |
| Rat laminin β1 chain | NP_001100191 | NM_001106721 |
| Rat laminin γ1 chain | NP_446418 | NM_053966 |

Laminin E8 is a trimeric fragment formed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, and about 230 amino acids from the N-terminus are involved in the trimer formation. The β chain E8 generally consists of about 220 to 230 amino acids. The γ chain E8 generally consists of about 240 to 250 amino acids. The glutamic acid residue at the third position from the C-terminus of the γ chain E8 is essential for the cell adhesion activity of laminin E8 (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

The cell-growth regulatory molecule which constitutes the modified laminin of the present invention means an extracellular factor required for cell culture and growth. The specific examples include (i) cell adhesion molecules as extracellular matrices which bind to receptors on cell surfaces and thereby provide a scaffold for cells, and (ii) molecules which bind to growth factors and thereby regulate the localization and activity of growth factors (herein called "growth factor binding molecules"). The "growth factor," which the growth factor binding molecule is supposed to bind to, is synonymous with "proliferation factor." The growth factor is not particularly limited and may be any substance capable of promoting cellular growth, proliferation, differentiation, etc. The examples include EGF (epidermal growth factor), bFGF (basic fibroblast growth factor), TGF (transforming growth factor), IGF (insulin-like growth factor), PDGF (platelet-derived growth factor), VEGF (vesicular endothelial growth factor), HGF (hepatocyte growth factor) and NGF (nerve growth factor).

The cell adhesion molecule which constitutes the modified laminin of the present invention may be a molecule involved in cell-to-extracellular matrix adhesion or cell-to-cell adhesion. The cell adhesion molecule encompasses not only membrane proteins present in cell membranes but also extracellular matrices without particular limitation. The cell adhesion molecule which constitutes the modified laminin of the present invention may be a full-length cell adhesion molecule or a fragment having a cell adhesion domain thereof. Examples of the adhesion molecule include (a) cell adhesion molecules capable of binding to integrins,
(b) cell adhesion molecules capable of binding to membrane-bound proteoglycans,
(c) cell adhesion molecules capable of binding to discoidin domain receptors,
(d) cell adhesion molecules capable of binding to dystroglycans, and
(e) cell adhesion molecules capable of binding to cell surface sugar chains.

It is preferred that the adhesion molecule is one or more kinds selected from the above (a) to (e).

Examples of the cell adhesion molecules capable of binding to integrins include fibronectin, collagen, vitronectin, nephronectin, osteopontin, MAEG, tenascin, SVEP1, TGF-β1 latency associated peptide and TGF-β3 latency associated peptide. Examples of the cell adhesion molecules capable of binding to membrane-bound proteoglycans include fibronectin, vitronectin, nephronectin and laminin. Examples of the cell adhesion molecules capable of binding to dystroglycans include laminin. Examples of the cell adhesion molecules capable of binding to cell surface sugar chains include Concanavalin A, *Dolichos biflorus* agglutinin, *Arachis hypogaea* agglutinin, *Ricinus communis* agglutinin and wheat germ agglutinin. The examples listed above are non-limiting examples.

Preferable examples of the cell adhesion molecule which constitutes the modified laminin of the present invention include proteins having an Arg-Gly-Asp sequence in their molecules, such as fibronectin, vitronectin, nephronectin, osteopontin, MAEG, TGF-β1 latency associated peptide, TGF-β3 latency associated peptide and tenascin; type I collagen, type IV collagen and other collagen molecules; SVEP1; and intercellular adhesion molecules of the cadherin family, such as E-cadherin, N-cadherin and P-cadherin. Examples of the fragment having a cell adhesion domain of the full-length cell adhesion molecule include a fragment having the 7th to 10th type III modules of human fibronectin (Fusao Kimizuka, Yoichi Ohdate, Yasutoshi Kawase, Tomoko Shimojyo, Yuki Taguchi, Kimikazu Hashino, ShoichiGoto, Hidetaka Hashi, Ikunoshin Kato, Kiyotoshi Sekiguchi, and Koiti Titani, "Role of type III homology repeats in cell adhesive function within the cell-binding domain of fibronectin" The Journal of Biological Chemistry, 266, 3045-3051, 1999), a fragment having the 12th to 14th type III modules of fibronectin (Ri-ichiroh Manabe, Naoko Oh-e, Toshinaga Maeda, Tomohiko Fukuda, and Kiyotoshi Sekiguchi, "Modulation of cell adhesive activity of fibronectin by the alternatively spliced EDA segment" The Journal of Cell Biology, 139, 295-307, 1997), and the central linker segment of nephronectin (Yuya Sato, Toshihiko Uemura, Keisuke Morimitsu, Ryoko Sato-Nishiuchi, Ri-ichiroh Manabe, Junichi Takagi, Masashi Yamada, and Kiyotoshi Sekiguchi, "Molecular basis of the recognition of nephronectin by integrin α8β1" The Journal of Biological Chemistry, 284, 14524-14536, 2009). Further, the globular domains 4 and/or 5 of the human laminin α chain can preferably be used as the cell adhesion molecule which constitutes the modified human laminin of the present invention.

The method for producing the cell adhesion molecule is not particularly limited. For example, the cell adhesion molecule can be obtained by purification from cells expressing the cell adhesion molecule of interest. Alternatively, the cell adhesion molecule can be produced as a recombinant protein. Recombinant proteins can be produced by appropriate known recombinant techniques. The nucleotide and amino acid sequence data of the genes encoding human fibronectin, vitronectin, nephronectin, osteopontin, MAEG, TGF-β1, TGF-β3, tenascin, type I collagen, type IV collagen, SVEP1, E-cadherin, N-cadherin and P-cadherin can be obtained from known databases (GenBank etc.) with the use of the respective accession numbers shown in Table 3. The nucleotide and amino acid sequence data of the genes of cell adhesion molecules derived from non-human organisms can also be obtained from known databases (GenBank etc.). As an example, the nucleotide and amino acid sequence data of the genes of lectins derived from non-human organisms among the cell adhesion molecules capable of binding to cell surface sugar chains are shown in Table 4.

TABLE 3

| | Amino acid sequence | Nucleotide sequence |
|---|---|---|
| Human fibronectin | NP_002017 | NM_002026 |
| Human vitronectin | NP_000629 | NM_000638 |
| Human nephronectin | NP_001171620 | NM_001184691 |
| Human osteopontin | NP_001035147 | NM_001040058 |
| Human MAEG | NP_001161362 | NM_001167890 |
| Human TGF-β1 | NP_000651 | NM_000660 |
| Human TGF-β3 | NP_003230 | NM_003239 |
| Human tenascin | NP_002151 | NM_002160 |
| Human type I collagen α1 chain | NP_000079 | NM_000088 |
| Human type I collagen α2 chain | NP_000080 | NM_000089 |
| Human type IV collagen α1 chain | NP_001836 | NM_001845 |
| Human type IV collagen α2 chain | NP_001837 | NM_001846 |
| Human SVEP1 | NP_699197 | NM_153366 |
| Human E-cadherin | NP_004351 | NM_004360 |
| Human N-cadherin | NP_001783 | NM_001792 |
| Human P-cadherin | NP_001784 | NM_001793 |

TABLE 4

| | Amino acid sequence | Nucleotide sequence |
|---|---|---|
| Concanavalin A | P02866 | X01632 |
| *Dolichos biflorus* agglutinin | P05045 | J02721 |
| *Arachis hypogaea* agglutinin | P02872 | S42352 |
| *Ricinus communis* agglutinin-1 | XP_002534649 | XM_002534603 |
| Wheat germ agglutinin | P10968 | M25536 |

The growth factor binding molecule which constitutes the modified laminin of the present invention may be any molecule capable of binding to growth factors involved in the growth of culture cells, and is not particularly limited. A chimerized growth factor binding molecule captures growth factors onto the matrix surface and allows the growth factors to more efficiently (physiologically) act on cells and to stimulate cell growth. The growth factor binding molecule which constitutes the modified laminin of the present invention may be a full-length, growth factor binding molecule or a fragment having a growth factor binding domain thereof.

Examples of the growth factor binding molecule include heparan sulphate proteoglycans. Examples of the heparan sulphate proteoglycans include perlecan, agrin, type XVIII collagen, syndecans 1 to 4 and glypicans 1 to 6. Examples of the growth factor binding molecule other than heparan sulphate proteoglycans include latent TGF-β binding proteins 1 to 4. Examples of the fragment having a growth factor binding domain of the full-length, growth factor binding molecule include the domains I to III of perlecan (the region from valine at the 22nd position to proline at the 1676th position from the N-terminus; the amino acid sequence data are shown in Table 5), and a region having the 1st to 8th follistatin (FS) domains of agrin (Uwe Winzen, Gregory J. Cole, and Willi Halfter, "Agrin is a chimeric proteoglycan with the attachment sites for heparan sulfate/chondroitin sulfate located in two multiple serine-glycine clusters" The Journal of Biological Chemistry, 278, 30106-30114, 2008).

The method for producing the growth factor binding molecule is not particularly limited. For example, the growth factor binding molecule can be obtained by purification from cells expressing the growth factor binding molecule of interest. Alternatively, the growth factor binding molecule can be produced as a recombinant protein. Recombinant proteins can be produced by appropriate known recombinant techniques. The nucleotide and amino acid sequence data of the genes encoding human perlecan, agrin, type XVIII collagen, syndecans 1 to 4, glypicans 1 to 6, and latent TGF-β binding proteins 1 to 4 can be obtained from known databases (GenBank etc.) with the use of the respective accession numbers shown in Table 5.

TABLE 5

| | Amino acid sequence | Nucleotide sequence |
|---|---|---|
| Human perlecan | NP_005520 | NM_005529 |
| Human agrin | NP_940978 | NM_198576 |
| Human type XVIII collagen α1 chain | NP_085059 | NM_030582 |
| Human syndecan 1 | NP_001006947 | NM_001006946 |
| Human syndecan 2 | NP_002989 | NM_002998 |
| Human syndecan 3 | NP_055469 | NM_014654 |
| Human syndecan 4 | NP_002990 | NM_002999 |
| Human glypican 1 | NP_002072 | NM_002081 |
| Human glypican 2 | NP_689955 | NM_152742 |
| Human glypican 3 | NP_001158089 | NM_001164617 |
| Human glypican 4 | NP_001439 | NM_001448 |
| Human glypican 5 | NP_004457 | NM_004466 |
| Human glypican 6 | NP_005699 | NM_005708 |
| Human latent TGF-β binding protein 1 | NP_996826 | NM_206943 |
| Human latent TGF-β binding protein 2 | NP_000419 | NM_000428 |
| Human latent TGF-β binding protein 3 | NP_001123616 | NM_001130144 |
| Human latent TGF-β binding protein 4 | NP_001036009 | NM_001042544 |

In the modified laminin of the present invention, the above-described cell-growth regulatory molecule (for example, cell adhesion molecules, growth factor binding molecules, etc.) is bound to at least one site selected from the α chain N-terminus, the α chain C-terminus, the β chain N-terminus and the γ chain N-terminus of laminin or a heterotrimeric laminin fragment. Therefore, in the modified laminin of the present invention, the cell-growth regulatory molecules may be bound to two, three or four sites. In the case where the cell-growth regulatory molecules are bound to more than one site, the cell-growth regulatory molecules may be of one kind, or two or more kinds. The cell-growth regulatory molecule may be bound to any of the four sites set forth above, but to the α chain C-terminus, the globular domains 4 and/or 5 of the laminin α chain are/is preferably bound.

The modified laminin of the present invention can be produced as a recombinant modified laminin by appropriate known recombinant techniques. For example, a modified laminin having a cell-growth regulatory molecule bound to the α chain N-terminus of human laminin E8 can be prepared as follows. First, a DNA encoding human laminin α chain E8 and a DNA encoding a cell-growth regulatory molecule are ligated to give a fusion gene encoding a fusion protein in which the cell-growth regulatory molecule is bound to the α chain N-terminus of human laminin E8, and the fusion gene is inserted into an appropriate vector to give an expression vector. Subsequently, this expression vector, an expression vector for human laminin β chain E8 and an expression vector for human laminin γ chain E8 are co-transfected into appropriate host cells, and the expressed trimeric protein is purified by a known method. In a similar manner, modified laminins having a cell-growth regulatory molecule bound to another site, and modified laminins having a cell-growth regulatory molecule bound to more than one site can also be produced. In the modified laminin of the present invention, a cell-growth regulatory molecule may be chemically bound to at least one site selected from the α chain N-terminus, the α chain C-terminus, the β chain N-terminus and the γ chain N-terminus.

The modified laminin of the present invention is highly active for cell adhesion and/or growth stimulation and can be provided as a highly pure and homogeneous protein. Therefore, the modified laminin of the present invention is very useful as an extracellular matrix for culture cells, in particular culture stem cells. Using a modified laminin of human origin as the modified laminin of the present invention enables culture of human stem cells in a feeder-free and xeno-free environment, and the thus-cultured cells can be provided as highly safe human stem cells applicable to regenerative medicine.

<Method for Culturing Mammalian Cells>

The present invention provides a method for culturing mammalian cells in the presence of the above-described modified laminin of the present invention. Since the modified laminin of the present invention is highly active for cell adhesion and/or growth stimulation, using the modified laminin as an extracellular matrix providing a scaffold for mammalian cells enables feeder-free culture of cells that are conventionally cultured with feeder cells.

The culture method of the present invention is applicable to culture of any mammalian cells, but is preferably applied to culture of stem cells. The stem cells refer to cells having the self-renewal capacity and pluripotency, and include somatic stem cells and pluripotent stem cells. Examples of the somatic stem cells include neural stem cells, mesenchymal stem cells and hematopoietic stem cells. Examples of the pluripotent stem cells include ES cells (embryonic stem cells), iPS cells (induced pluripotent stem cells), mGS cells (multipotent germ stem cells) and hybridomas of ES cells and somatic cells. Pluripotent stem cells are more preferred, and ES cells or iPS cells are still more preferred. The mammal as the origin of the cells is not particularly limited, and the examples include humans, mice, rats, cattle and pigs. Particularly preferred are humans. That is, the culture method of the present invention is preferably used for human stem cell culture. In the case where human stem cells are cultured according to the culture method of the present invention, the modified laminin of human origin is preferably used.

The method for culturing mammalian cells in the presence of the modified human laminin may be a culture method using a culture medium containing the modified laminin of the present invention, or a culture method using a culture substrate coated with the modified laminin of the present invention. In the case where a culture medium containing the modified laminin of the present invention is used, the modified laminin may be added to a culture medium in advance or just before use. The amount of the modified laminin to be added is not particularly limited, but the amount of the modified laminin relative to the usable area of the culture substrate is preferably about 0.03 to 25 μg/cm$^2$, more preferably about 0.06 to 10 μg/cm$^2$, and still more preferably about 0.38 to 3.8 μg/cm$^2$.

Hereinafter, as an embodiment of the culture method of the present invention, a method for culturing human stem cells in the presence of the modified laminin of human origin is described, but the culture method of the present invention is not limited to this exemplary method and can preferably be used for non-human mammalian cell culture as well.

In the case where human stem cells are cultured according to the culture method of the present invention, the culture medium used is not particularly limited, but preferred are synthetic media, and particularly preferred are synthetic media free from ingredients derived from non-human organisms (that is, xeno-free). Human stem cells cultured in feeder-free and xeno-free conditions according to the culture method of the present invention can be provided as highly safe human stem cells applicable to regenerative medicine. Synthetic media are commercially available, and commercial products can preferably be used. Examples of the commercially available synthetic media include mTeSR1 (trade name, STEMCELL TECHNOLOGIES), TeSR2 (trade name, STEMCELL TECHNOLOGIES), StemPro hESC SFM (trade name, Invitrogen) and hESF-GRO (trade name, Cell Science & Technology Institute, Inc.). Among these, TeSR2 is a xeno-free culture medium. The culture media described in the following References (i) to (v) can also be preferably used.

(i) Liu, Y. et al., Biochem. Biophys. Res. Commun., 346: 131-139, 2006.
(ii) Vallier, L. et al., J. Cell Sci. 118: 4495-4509, 2005.
(iii) Li, Y. et al., Biotechnol. Bioeng., 91: 688-698, 2005.
(iv) Yao, S. et al., Proc. Natl. Acad. Sci. U.S.A., 103: 6907-6912, 2006.
(v) Lu, J. et al., Proc. Natl. Acad. Sci. U.S.A., 103: 5688-5693, 2006.

An embodiment in which human iPS cells are cultured according to the culture method of the present invention is described below.

(1) Collection of Human iPS Cells from Co-Culture System with Feeder Cells

Human iPS cells are collected from a co-culture system with feeder cells according to the following method 1 or 2.

Method 1:

To a culture dish in which human iPS cells have been co-cultured with feeder cells (for example, MEFs) (Day 3 to Day 5), 0.25% trypsin/DMEM-F12 (for example, 1 ml/60 mm dish) is added, and incubation was performed at 37° C. for 2 to 3 minutes for enzymatic treatment. The culture dish is washed with DMEM-F12 and thereby feeder cells are removed. Then, a culture medium is added to the culture dish and the cells on the entire culture dish are physically detached. The resulting cell suspension is filtered through a BD Falcon 100-μm cell strainer (BD Falcon #352460) and the strainer is washed. As a result, only human iPS cell colonies are separated and collected.

Method 2:

To a culture dish in which human iPS cells have been co-cultured with feeder cells (for example, MEFs) (Day 3 to Day 5), a cell detachment solution (for example, Dissociation Solution for ES/iPS Cells (RCHETP002, ReproCELL Inc.), 1 mg/ml dispase/DMEM-F12, 10 mg/ml collagenase IV/DMEM-F12, etc.) (for example, 1 ml/60 mm dish) is added, and incubation was performed at 37° C. for 5 minutes for enzymatic treatment. As a result, the human iPS cells and MEFs are detached from the culture dish. Then, the detached cells are transferred into a 15-ml centrifuge tube. To this tube, about 10 ml of a culture medium is added, the cells are suspended, the tube is left to stand for 5 minutes to allow only the colonies to precipitate, and then the supernatant is removed. By repeating this procedure twice or more, only human iPS cell colonies are collected.

(2) Transfer of Human iPS Cells onto Culture Substrate Coated with Modified Laminin of Human Origin The collected human iPS cell colonies are dissociated into single cells. The method for dissociating the colonies into single cells is not particularly limited, and the examples include trypsinization and also include several times of flushing in a culture medium using a Pipetman P-1000 or the like. The cells dissociated into single cells are resuspended in an appropriate culture medium (for example, TeSR2 etc.), and seeded on a culture dish coated with the modified laminin of human origin (for example, 1.0 μg/cm$^2$). The culture is performed in a $CO_2$ concentration suitable for the culture medium used, and the culture medium is replaced daily.

(3) Passage Culture

Passage is performed at the time when the space for further cell expansion becomes short or cell death becomes noticeable in the colonies. In the culture method of the present invention, passage may be performed by seeding human iPS cells in the form of moderate-sized colonies, as in conventional methods. Alternatively, passage may be performed by seeding human iPS cells dissociated into single cells. Here, the state of "dissociated into single cells" means not only a state in which all the cells in a cell suspension are present as single cells, but also a state in which some cells in a cell suspension are present as single cells and other cells therein are present in an aggregate form of about several to a little more than ten cells.

In the Case of Cells Dissociated into Single Cells:

To a culture dish in which human iPS cells have been cultured, TrypLE Select (trade name, Invitrogen #12563011) (for example, 1 ml/100 mm dish) is added, and incubation was performed at 37° C. for 5 minutes for enzymatic treatment. The human iPS cell colonies are dissociated into single cells, for example, by several times of flushing in a culture medium using a Pipetman P-1000 or the like. After addition of a culture medium, the human iPS cells are suspended and then collected in a centrifuge tube. After the step of centrifugation (1000×g, 3 minutes) and subsequent washing with a culture medium is repeated twice, the human iPS cells are resuspended in a fresh culture medium and seeded in a single-cell state at a cell density of, for example, about 40,000 cells/cm$^2$ on a culture dish coated with the modified laminin of human origin (for example, 1.0 μg/cm$^2$). The culture is performed in a $CO_2$ concentration suitable for the culture medium used, and the culture medium is replaced daily.

In the Case of Cells not Dissociated into Single Cells:

In this case, collagenase IV, dispase, accutase or the like is used as the enzyme for cell detachment. To a culture dish in which human iPS cells have been cultured, 10 mg/ml collagenase/DMEM-F12, 2 mg/ml dispase/DMEM-F12 or accutase (Millipore #SCR005) (for example, 1 ml/60 mm dish) is added, and incubation was performed at 37° C. for 5 minutes for enzymatic treatment. After removal of the enzyme solution, a culture medium is added, and the human iPS cell colonies are split into smaller-sized colonies composed of about 50 to 100 cells, for example, by several times of flushing in a culture medium using a Pipetman P-1000 or the like. The cell suspension is collected in a centrifuge tube. After the step of centrifugation (200×g, 3 minutes) and subsequent washing with a culture medium is repeated twice, the human iPS cells are resuspended in a fresh culture medium and seeded in a 2- to 4-fold dilution on a culture dish coated with the modified laminin of human origin (for example, 1.5 μg/cm$^2$). The culture is performed in a $CO_2$ concentration suitable for the culture medium used, and the culture medium is replaced daily.

<Method for Establishing iPS Cells>

The present invention provides a method for establishing iPS cells in the presence of the above-described modified laminin of the present invention. The method of the present invention for establishing iPS cells comprises the step of bringing a nuclear reprogramming substance into contact with somatic cells in the presence of the above-described modified laminin of the present invention. Preferably, the method of the present invention for establishing iPS cells further comprises the step of culturing, in the presence of the modified laminin of the present invention, the somatic cells which have been in contact with the nuclear reprogramming substance.

It is known that iPS cells can be established according to certain procedures, for example, the procedures described in the following.

(vi) Takahashi, K. and Yamanaka, S., Cell, 126: 663-676 (2006)
(vii) Okita, K. et al., Nature, 448: 313-317 (2007)
(viii) Wernig, M. et al., Nature, 448: 318-324 (2007)
(ix) Maherali, N. et al., Cell Stem Cell, 1: 55-70 (2007)
(x) Nakagawa, M. et al., Nat. Biotethnol., 26: 101-106 (2008)
(xi) Takahashi, K. et al., Cell, 131: 861-872 (2007)
(xii) Yu, J. et al., Science, 318: 1917-1920 (2007)
(xiii) Maekawa, M. et al., Nature, 474: 225-229 (2011)

As shown in these references, human or mouse iPS cells equivalent to ES cells in pluripotency can be generated by introduction of specific factors into somatic cells. The "specific factor" is defined as a "nuclear reprogramming substance" in the present invention. The nuclear reprogramming substance may be composed of any substance(s) as long as iPS cells can be generated by introducing the substance(s) into somatic cells or by bringing the substance(s) and an agent for improving the efficiency of generating iPS cells into contact with somatic cells. The examples of such a substance(s) include protein factors, nucleic acids encoding the same (which may be present in vectors) and low molecular weight compounds.

In the case where the nuclear reprogramming substance is a protein factor or a nucleic acid encoding the same, the combinations shown below are preferable examples (in the following, only the names of protein factors are given).

(1) Oct3/4, Klf4, c-Myc
(2) Oct3/4, Klf4, c-Myc, Sox2 (Sox2 can be replaced with Sox1, Sox3, Sox15, Sox17 or Sox18; Klf4 can be replaced with Klf1, Klf2 or Klf5; and c-Myc can be replaced with T85A mutant (active form) or L-Myc)
(3) Oct3/4, Klf4, c-Myc, Sox2, Fbx15, Nanog, ERas, Tcell
(4) Oct3/4, Klf4, c-Myc, Sox2, TERT, SV40 Large T antigen (hereinafter referred to as SV40 LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmil (regarding the above combinations, see WO 2007/069666 (regarding the replacement of Sox2 with Sox18 and the replacement of Klf4 with Klf1 or Klf5 in the combination in the above (2), see Nature Biotechnology, 26, 101-106 (2008)); regarding the combination of Oct3/4, Klf4, c-Myc and Sox2, see also Cell, 126, 663-676 (2006), Cell, 131, 861-872 (2007), etc.; regarding the combination of Oct3/4, Klf4 (or Klf5), c-Myc and Sox2, see also Nat. Cell Biol., 11, 197-203 (2009); and regarding the combination of Oct3/4, Klf4, c-Myc, Sox2, hTERT and SV40 LT, see also Nature, 451, 141-146 (2008))
(9) Oct3/4, Klf4, Sox2 (see Nature Biotechnology, 26, 101-106 (2008))
(10) Oct3/4, Sox2, Nanog, Lin28 (see Science, 318, 1917-1920 (2007))
(11) Oct3/4, Sox2, Nanog, Lin28, hTERT, SV40 LT (see Stem Cells, 26, 1998-2005 (2008))
(12) Oct3/4, Klf4, c-Myc, Sox2, Nanog, Lin28 (see Cell Research (2008) 600-603)
(13) Oct3/4, Klf4, c-Myc, Sox2, SV40 LT (see also Stem Cells, 26, 1998-2005 (2008))
(14) Oct3/4, Klf4 (see Nature 454: 646-650 (2008) and Cell Stem Cell, 2: 525-528 (2008))
(15) Oct3/4, c-Myc (see Nature 454:646-650 (2008))
(16) Oct3/4, Sox2 (see Nature, 451, 141-146 (2008) and WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (Esrrb can be replaced with Esrrg; see Nat. Cell Biol., 11, 197-203 (2009))
(20) Oct3/4, Sox2, Esrrb (see Nat. Cell Biol., 11, 197-203 (2009))
(21) Oct3/4, Klf4, L-Myc (see Proc. Natl. Acad. Sci. USA., 107, 14152-14157 (2010))
(22) Oct3/4, Nanog
(23) Oct3/4 (see Cell 136: 411-419 (2009) and Nature, 08436, doi:10.1038 published online (2009))
(24) Oct3/4, Klf4, c-Myc, Sox2, Nanog, Lin28, SV4OLT (see Science, 324: 797-801 (2009))
(25) Oct3/4, Klf4, Sox2, c-Myc, Glis1 (see Nature, 474: 225-229 (2011), WO2010/098419 and WO2011/102531)
(26) Oct3/4, K1f4, Sox2, Glis1 (see Nature, 474: 225-229 (2011), WO2010/098419 and WO2011/102531)

In the above (1) to (26), in place of Oct3/4, other members of the Oct family, for example, Oct1A, Oct6 and the like, are usable. In place of Sox2 (or Sox1, Sox3, Sox15, Sox17, Sox18), the other members of the Sox family, for example, Sox7 and the like are usable. In place of Glis1, the other members of the Glis family such as Glis2 and Glis3 are usable. In the case where c-Myc or Lin28 is present as a nuclear reprogramming substance in the above (1) to (26), c-Myc and Lin28 can be replaced with L-Myc and Lin28B, respectively.

Further, combinations which do not correspond to those in the above (1) to (26) but contain all the components in any one of the above (1) to (26) and some other substance can be included in the "nuclear reprogramming substance" used in the present invention. Furthermore, when a part of the components in any one of the above (1) to (26) are endogenously expressed in somatic cells at a sufficient level required for nuclear reprogramming, combinations of only the other components can also be included in the "nuclear reprogramming substance" used in the present invention.

Among all the above combinations, combinations of at least one, preferably two or more, and more preferably three or more selected from Oct3/4, Sox2, Klf4, L-Myc, Lin28 and Glis1 are preferred as an example of the nuclear reprogramming substance.

The mouse and human cDNA sequence data of the above-mentioned protein factors can be obtained with reference to the NCBI accession numbers shown in WO 2007/069666 (Nanog is described as "ECAT4" in this literature, and the mouse and human cDNA sequence data of Lin28, Lin28B, Esrrb, Esrrg, L-Myc and Glis1 can be obtained with reference to the NCBI accession numbers shown in Table 6). The skilled person can easily isolate cDNAs of these protein factors.

TABLE 6

| Gene name | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |
| Glis1 | NM_147221 | NM_147193 |

In the case where the nuclear reprogramming substance capable of inducing the generation of iPS cells is a protein factor, the introduction of the protein factor into somatic cells can be performed by a method known per se for introducing proteins into cells. The examples include a method using a protein transfection reagent, a method using a protein transduction domain or a cell permeable peptide fusion protein, and a microinjection method. In addition, other methods, such as an electroporation method, a semi-intact cell method (Kano, F. et al. Methods in Molecular Biology, Vol. 322, 357-365 (2006)), and a transfection method using a Wr-t peptide (Kondo, E. et al., Mol. Cancer Ther. 3 (12), 1623-1630 (2004)) can also be used. When the efficiency of generating iPS cells is regarded as important, it is preferable that, rather than protein factors, nucleic acids encoding the same are used as the nuclear reprogramming substance. The nucleic acid may be DNA, RNA or a DNA/RNA chimera, and the nucleic acid may be a double or single strand. Preferably, the nucleic acid is a double-stranded DNA, in particular cDNA. The cDNA as the nuclear reprogramming substance is inserted in a suitable expression vector containing a promoter that can function in host somatic cells. Examples of the expression vector include viral vectors such as retrovirus, lentivirus, adenovirus, adeno-associated virus, herpes virus and sendai virus; and animal cell expression plasmids (for example, pA-11, pxT1, pRc/CMV, pRc/RSV and pcDNAI/Neo). The kind of vector to be used is appropriately selected depending on the application of iPS cells. For example, adenovirus vectors, plasmid vectors, adeno-associated virus vectors, retrovirus vectors, lentivirus vectors, sendai virus vectors, etc. can be used. The nucleic acids used as the nuclear reprogramming substance (reprogramming genes) may be individually inserted into separate expression vectors, and alternatively, two or more kinds, preferably two to three kinds of genes may be inserted into one expression vector. The former is preferred in the case where retrovirus or lentivirus vectors with high transfection efficiency are used, and the latter is preferred in the case where plasmid vectors, adenovirus vectors, episomal vectors or the like are used. Further, an expression vector having two or more kinds of genes inserted therein and an expression vector having only one kind of gene inserted therein can be used in combination.

<Method for Rapid Expansion of Stem Cells>

The present invention provides a method for rapid expansion of stem cells. The rapid expansion method of the present invention comprises the steps of dissociating stem cells into single cells, and culturing the stem cells dissociated into single cells in the presence of the above-described modified laminin of the present invention, the stem cells dissociated into single cells being seeded at a cell density of about $2\times10^4$ to $20\times10^4$ cells/cm$^2$. The seeding density is more preferably about $3\times10^4$ to $10\times10^4$ cells/cm$^2$, and still more preferably about $4\times10^4$ to $5\times10^4$ cells/cm$^2$. When stem cells dissociated into single cells are seeded at the above density, the adhesion efficiency in conventional culture systems is very low, but according to the rapid expansion method of the present invention, the adhesion efficiency is significantly higher, the stem cells can grow vigorously, and therefore remarkably higher speed growth of the stem cells than that in conventional methods can be achieved.

In the step of dissociating stem cells into single cells, as in the above "In the case of cells dissociated into single cells," stem cell colonies are detached and collected from a culture dish, and these colonies are dissociated into single cells, for example, by trypsinization or by several times of flushing in a culture medium using a Pipetman P-1000 or the like. Then, the cell number is counted by a known cell counting method, and the cell concentration of the cell suspension is appropriately adjusted to provide the above-mentioned seeding density. The culturing step can be performed according to the description in the culture method of the present invention.

The method of the present invention for rapid expansion of stem cells is preferably applied to pluripotent stem cells such as ES cells and iPS cells, and more preferably ES cells. The method of the present invention for rapid expansion of stem cells is preferably applied to human pluripotent stem cells, and more preferably human ES cells. In the case where the method of the present invention for rapid expansion of stem cells is applied to human stem cells, the modified laminin of human origin is preferably used.

<Separation Method for Single-Cell-Derived Clones of Stem Cells>

The present invention provides a separation method for single-cell-derived clones of stem cells. The separation method of the present invention comprises the steps of dissociating stem cells into single cells, and culturing the stem cells dissociated into single cells in the presence of the above-described modified laminin of the present invention, and the method is characterized by formation of single-cell-derived colonies. According to the separation method of the present invention, unlike in conventional culture systems, single-cell-derived clones of stem cells can be easily formed and separated, and thus homogeneous stem cells can be easily obtained.

For the formation of single-cell-derived colonies and the separation of single-cell-derived clones, any method may be used without particular limitation, and for example, a known limiting dilution etc. can preferably be used. Depending on the method used, the cell density and the culture substrate to be used are appropriately selected, and under the selected conditions, human stem cells dissociated into single cells are seeded and cultured. The culturing step can be performed according to the description in the culture method of the present invention.

The separation method for single-cell-derived clones of stem cells is preferably applied to pluripotent stem cells such as ES cells and iPS cells, and more preferably ES cells. The separation method for single-cell-derived clones of stem cells is preferably applied to human pluripotent stem cells, and more preferably human ES cells. In the case where the separation method for single-cell-derived clones of stem cells is applied to human stem cells, the modified laminin of human origin is preferably used.

<Single-Cell Culture Method for Stem Cells>

The present invention provides a single-cell culture method for stem cells. The single-cell culture method of the present invention comprises the steps of dissociating stem cells into single cells, and culturing the stem cells dissociated into single cells in the presence of the above-described modified laminin of the present invention, and the method is characterized by maintenance of the stem cells in a single-cell state without growth. Generally, in the colony formed of stem cells, the cells at the edge of the colony may be different in cell condition from those inside the colony, but according to the single-cell culture method of the present invention, stem cells do not form colonies and thus can be obtained in a uniform condition, and enhancement in the efficiency of differentiation induction can be expected.

For the maintenance of the stem cells in a single-cell state without growth, it is preferable that the stem cells dissociated into single cells are seeded at an appropriate cell density selected depending on the culture substrate and then used up for other applications before the cells grow. Also, for prolonged maintenance of the stem cells in a single-cell state, for example, a culture medium with no or less growth factor may be used.

The single-cell culture method of the present invention is preferably applied to pluripotent stem cells such as ES cells and iPS cells, and more preferably ES cells. The single-cell culture method of the present invention is preferably applied to human pluripotent stem cells, and more preferably human ES cells. In the case where the single-cell culture method of the present invention is applied to human stem cells, the modified laminin of human origin is preferably used.

<Culture Substrate>

The present invention provides a culture substrate coated with the above-described modified laminin of the present invention. The cells to be cultured with the use of the culture substrate of the present invention are not particularly limited and may be any mammalian cells that can be cultured. Preferred are stem cells. The stem cells include somatic stem cells and pluripotent stem cells. Examples of the somatic stem cells include neural stem cells, mesenchymal stem cells and hematopoietic stem cells. Examples of the pluripotent stem cells include ES cells (embryonic stem cells), iPS cells (induced pluripotent stem cells), mGS cells (multipotent germ stem cells) and hybridomas of ES cells and somatic cells. Pluripotent stem cells are more preferred, and ES cells or iPS cells are still more preferred. Examples of the mammal as the origin of the cells include humans, mice, rats, cattle and pigs. Particularly preferred are humans. The culture substrate of the present invention is very useful for feeder-free culture of cells that are conventionally cultured with feeder cells.

The method for producing the culture substrate of the present invention is not particularly limited and may be any method that is usable for coating of a known culture substrate with the modified laminin of the present invention. For example, the above-described modified laminin of the present invention is diluted with a suitable solvent, such as PBS, physiological saline and a physiological saline adjusted to a neutral pH with tris(hydroxymethyl)aminomethane or 4-(2-hydroxyethyl)-1-piperazine ethanesulfonic acid, the diluted solution is added to a suitable culture substrate, and the culture substrate is left to stand at about 4 to 37° C. for about 1 to 12 hours. As a result, the culture substrate is coated with the modified laminin and thus the culture substrate of the present invention can be produced. The culture substrate to be coated is not limited as long as it can be used for mammalian cell culture, and the examples include glass or plastic dishes, flasks, multiwell plates, culture slides and microcarriers, and polymer membranes such as a polyvinylidene fluoride membrane.

The coating concentration of the modified laminin is not particularly limited, but preferably about 0.03 to 25 μg/cm$^2$, more preferably about 0.06 to 10 μg/cm$^2$, and still more preferably about 0.38 to 3.8 μg/cm$^2$. Since the culture substrate of the present invention uses the modified laminin of the present invention, a larger number of human stem cells can adhere and grow thereon even if the coating concentration is lower than that of conventionally used Matrigel.

In the culture substrate of the present invention, the modified laminin of the present invention used for coating may be of one kind, or two or more kinds. In addition to the modified laminin, other components may be used for coating. Examples of such components include serum components, extracellular matrix molecules, growth factors, differentiation inducing factors and morphogenetic factors (morphogens). Non-biological components, such as synthetic polymer gel (synthetic polymer), may also be used for coating.

In the culture substrate of the present invention, the modified laminin of human origin is preferably used for coating. In this case, it is preferred that the other coating components as described above are also human-derived components. The culture substrate coated with the modified laminin of human origin enables maintenance culture of human stem cells while supporting their pluripotency in an environment without feeder cells (feeder-free environment), which are usually used for human stem cell culture. In human stem cell culture, a co-culture system with feeder cells, such as mouse embryonic fibroblasts (MEFs) whose growth has been arrested by X-ray radiation or mitomycin-C treatment, is usually employed for maintenance of clonal growth and undifferentiated state of human stem cells. A culture system without such feeder cells is called a feeder-free culture system. Further, using a culture medium without xenogeneic components enables culture of human stem cells in conditions completely free from xenogeneic components (xeno-free culture conditions), and the thus-cultured cells can be provided as highly safe human stem cells with a very low risk of developing immunogenicity in humans. Examples of xeno-free culture media include TeSR2 (trade name, STEMCELL TECHNOLOGIES).

EXAMPLES

Hereinafter, the present invention will be illustrated in detail by Examples, but is not limited thereto.

Example 1

Preparation of Modified Human Laminin (1) Preparation of Expression Vector for Plus#1 Laminin E8

For preparation of Plus#1 laminin E8 (a modified human laminin in which the 4th and 5th globular domains of the human laminin α1 chain are fused with the E8 fragment of recombinant human laminin α5β1γ1), recombinant human laminin 511E8 (hereinafter referred to as "rhLM511E8") was first prepared, and then to the C-terminal region of the human laminin α5 chain E8, the 4th and 5th globular domains of the human laminin α1 chain (hereinafter referred to as "human laminin α1 chain LG45") were added.

(1-1) Construction of Expression Vectors for Human Laminin α5, β1 and γ1 Chain E8 Fragments rhLM511E8 was prepared according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins", The Journal of Biological Chemistry, 282, 11144-11154, 2007) as follows.

First, PCR was performed using a cloning plasmid pBluescript KS(+) (Stratagene) as a template to prepare three kinds of pBluescript KS(+) containing a DNA encoding a 6×His tag (HHHHHH), a DNA encoding an HA (hemagglutinin) tag (YPYDVPDYA) or a DNA encoding a FLAG tag (DYKDDDDK) inserted at the 5' end of the EcoRV site in the multicloning site. The three sets of primers used for the PCR are as follows.

```
(i)  Primers for 6×His tag insertion
                              (forward, SEQ ID NO: 1)
     5'-ATGATGATGAAGCTTATCGATACCGT-3'

(reverse, SEQ ID NO: 2)
     5'-CATCATCATGATATCGAATTCCTGCA-3'

(ii) Primers for HA tag insertion
                              (forward, SEQ ID NO: 3)
     5'-ATCATATGGATAAAGCTTATCGATACCGT-3'

(reverse, SEQ ID NO: 4)
     5'-GTGCCAGATTATGCAGATATCGAATTCCT-3'

(iii) Primers for FLAG tag insertion
                              (forward, SEQ ID NO: 5)
     5'-ATCCTTGTAATCAAGCTTATCGATACCGT-3'

(reverse, SEQ ID NO: 6)
     5'-GATGATGATAAGGATATCGAATTCCT-3'
```

Next, PCR was performed using plasmids containing the full-length nucleotide sequences of the α5, β1 and γ1 chains (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Comb, James M. Ervasti, and Kiyotoshi Sekiguchi, "Molecular Dissection of the α-Dystroglycan- and Integrin-binding Sites within the Globular Domain of Human Laminin-10", The Journal of Biological Chemistry, 279, 10946-10954, 2004) as templates to amplify the region corresponding to α5 (Ala$^{2534}$-Ala$^{3327}$), the region corresponding to β1 (Leu$^{1561}$-Leu$^{1786}$) and the region corresponding to γ1 (Asn$^{1362}$-Pro$^{1609}$), respectively. The primers used for the PCR are as follows.

```
(iv) Primers for amplification of α5 chain E8
     fragment
                              (forward, SEQ ID NO: 7)
     5'-GCTGCCGAGGATGCTGCTGGCCAGG-3'

(reverse, SEQ ID NO: 8)
     5'-CTAGGCAGGATGCCGGGCGGGCTGA-3'

(v)  Primers for amplification of β1 chain E8
     fragment
                              (forward, SEQ ID NO: 9)
     5'-CTTCAGCATAGTGCTGCTGACATTG-3'
```

```
                                            (reverse, SEQ ID NO: 10)
5'-TTACAAGCATGTGCTATACACAGCAAC-3'

(vi) Primers for amplification of γ1 chain E8
fragment
                                            (forward, SEQ ID NO: 11)
5'-AATGACATTCTCAACAACCTGAAAG-3'

(reverse, SEQ ID NO: 12)
5'-CTAGGGCTTTTCAATGGACGGGGTG-3'
```

The amplified DNA fragments were separately inserted into the EcoRV site in the multicloning site of the above-prepared three kinds of pBluescript KS(+) containing a tag-encoding sequence. From each resulting plasmid, the region containing the inserted DNA fragment and the 5'-terminal tag-encoding sequence was amplified. Then, the amplified product was digested with restriction enzymes EcoRI and HindIII. The digested fragment was inserted into the corresponding restriction site of pSecTag2B, a mammalian cell expression vector which contains a DNA sequence encoding the mouse Ig κ-chain V-J2-C signal peptide (Invitrogen), to give an expression vector for the human α5 chain E8 fragment (containing the 6×His tag in the N-terminal region), an expression vector for the human β1 chain E8 fragment (containing the HA tag in the N-terminal region), and an expression vector for the human γ1 chain E8 fragment (containing the FLAG tag in the N-terminal region) were prepared.

(1-2) Construction of Expression Vector for Human Laminin α1 Chain LG45-Fused Human Laminin α5 Chain E8 Fragment For preparation of a DNA fragment encoding a mouse Ig κ-chain V-J2-C signal peptide, a 6×His tag, human laminin α5 chain E8 and human laminin α1 chain LG45 in this order from the 5' end, a DNA fragment encoding human laminin α5 chain E8 and a DNA fragment encoding human laminin α1 chain LG45 were separately obtained, and these two kinds of DNA fragments were ligated and amplified by extension PCR. The amplified product was digested with a restriction enzyme AscI and inserted into the AscI-PmeI site of the expression vector for human laminin α5 chain E8 to give an expression vector for a human laminin α1 chain LG45-fused human laminin α5 chain E8 fragment.

First, PCR was performed using the expression vector for the human laminin α5 chain E8 fragment as a template to amplify the 754 base pairs from the 3' end of the α5 chain E8 fragment-encoding sequence. The primers used for the PCR are as below. The primer of SEQ ID NO: 14 contains a sequence for extension PCR in the 5'-terminal region.

```
(vii) Primers for amplification of human
laminin α5 chain partial fragment
                                            (forward, SEQ ID NO: 13)
5'-CAATGATCTGGAGCTGGCCGACGCCTACTACCTG-3'

(reverse, SEQ ID NO: 14)
5'-CTCTGCATCAGGCCCCAGGCCCGGGGTC-3'
```

Next, PCR was performed using a plasmid containing the full-length nucleotide sequence of the human laminin α1 chain (Hiroyuki Ido, Kenji Harada, Yoshiko Yagi, and Kiyotoshi Sekiguchi, "Probing the integrin-binding site within the globular domain of laminin-511 with the function-blocking monoclonal antibody 4C7.", Matrix Biology, 25 (2), 112-117, 2006) as a template to amplify the region corresponding to the human laminin α1 chain LG45 domain ($As^{2684}$-$Ser^{3075}$). The primers used for the PCR are as below.

The primer of SEQ ID NO: 15 contains a sequence for extension PCR in the 5'-terminal region.

```
(viii) Primers for amplification of human laminin
α1 chain LG45 domain
                                            (forward, SEQ ID NO: 15)
5'-CCTGGGGCCTGATGCAGAGGACAGCAA-3'

(reverse, SEQ ID NO: 16)
5'-AAACTCAGGACTCGGTCCCAGGACAGGAATGAAGG-3'
```

The obtained two kinds of DNA fragments were ligated and amplified by extension PCR using the primers shown below, to give a DNA fragment encoding the C-terminal region of human laminin α5 chain E8 and the human laminin α1 chain LG45 domain. The amplified DNA was digested with a restriction enzyme AscI and inserted into the AscI-PmeI site of the expression vector for human laminin α5 chain E8 to give an expression vector for a human laminin α1 chain LG45-fused human laminin α5 chain E8 fragment.

```
(ix) Primers for amplification of human laminin
α5 chain E8 C-terminal region and human laminin
α1 chain LG45 domain
                                            (forward, SEQ ID NO: 13)
5'-CAATGATCTGGAGCTGGCCGACGCCTACTACCTG-3

(reverse, SEQ ID NO: 16)
5'-AAACTCAGGACTCGGTCCCAGGACAGGAATGAAGG-3'
```

(2) Construction of Expression Vector for Plus#2 Laminin E8

For preparation of Plus#2 laminin E8 (a modified human laminin in which the 7th to 10th type III modules of human fibronectin are fused with rhLM511E8), rhLM511E8 was first prepared, and then to the N-terminal region of the human laminin γ1 chain E8, the cell adhesion domain of human fibronectin (the 7th to 10th type III modules of human fibronectin; hereinafter referred to as "FNIII7-10") was added.

(2-1) Construction of Expression Vectors for Human Laminin α5, β1 and γ1 Chain E8 Fragments In the same manner as in the above (1-1), an expression vector for the human laminin α5 chain E8 fragment (containing the 6×His tag in the N-terminal region), an expression vector for the human laminin β1 chain E8 fragment (containing the HA tag in the N-terminal region), and an expression vector for the human laminin γ1 chain E8 fragment (containing the FLAG tag in the N-terminal region) were prepared.

(2-2) Construction of Expression Vector for FNIII7-10-Fused Human Laminin γ1 E8 Fragment For preparation of a DNA fragment encoding a mouse Ig κ-chain V-J2-C signal peptide, a FLAG tag, FNIII7-10 and γ1 chain E8 in this order from the 5' end, a DNA fragment encoding a mouse Ig κ-chain V-J2-C signal peptide and a FLAG tag, a DNA fragment encoding FNIII7-10, and a DNA fragment encoding the γ1 chain E8 fragment were separately obtained, and these three kinds of DNA fragments were ligated and amplified by extension PCR. The amplified product was digested with restriction enzymes NheI and NotI. The digested fragment was inserted into the corresponding restriction site of pSecTag2B, a mammalian cell expression vector which contains a DNA sequence encoding the mouse Ig κ-chain V-J2-C signal peptide (Invitrogen), to give an expression vector for a FNIII7-10-fused human laminin γ1 E8 fragment.

First, PCR was performed using the expression vector for the human laminin γ1 chain E8 fragment as a template to amplify the region corresponding to the mouse Ig κ-chain V-J2-C signal peptide and the FLAG tag and the region corresponding to the γ1 chain E8 fragment. The primers used for the PCR are as below. The primers of SEQ ID NOS: 18 and 19 contain a sequence for extension PCR in the 5'-terminal region.

```
(x) Primers for amplification of signal peptide
sequence-FLAG tag sequence
                          (forward, SEQ ID NO: 17)
5'-GAGGTCTATATAAGCAGAGCTCTCTGGCTAACTA-3'

(reverse, SEQ ID NO: 18)
5'-TGGTGGAGACAATGGATCCTTATCATCATCATCC-3'

(xi) Primers for amplification of γ1 chain E8
fragment sequence
                          (forward, SEQ ID NO: 19)
5'-TAATTACCGAACAGATAATGACATTCTCAACAACC-3'

(reverse, SEQ ID NO: 20)
5'-GAAAGGACAGTGGGAGTGGCACC-3'
```

Next, PCR was performed using an expression vector for human fibronectin (Hiroki Akamatsu, Keiko Ichihara-Tanaka, Keiichi Ozono, Wataru Kamiike, Hikaru Matsuda, and Kiyotoshi Sekiguchi, "Suppression of Transformed Phenotypes of Human Fibrosarcoma Cells by Overexpression of Recombinant Fibronectin", Cancer Research, 56, 4541-4546, 1996) as a template to amplify the region corresponding to FNIII7-10 ($Pro^{1173}$-$Arg^{1539}$). The primers used for the PCR are as below. The primers of SEQ ID NOS: 21 and 22 contain a sequence for extension PCR in the 5'-terminal region.

```
(xii) Primers for amplification of FNIII7-10
sequence
                          (forward, SEQ ID NO: 21)
5'-GATGATGATAAGGATCCATTGTCTCCACCAACAA-3'

(reverse, SEQ ID NO: 22)
5'-ATGTCATTATCTGTTCGGTAATTAATGGAAATTGG-3'
```

The obtained three kinds of DNA fragments were ligated and amplified by extension PCR using the primers shown below, to give a DNA fragment encoding a mouse Ig κ-chain V-J2-C signal peptide, a FLAG tag, FNIII7-10 and γ1 chain E8. The amplified DNA was digested with restriction enzymes NheI and NotI. The digested fragment was inserted into the corresponding restriction site of a mammalian cell expression vector pSecTag2B (Invitrogen), to give an expression vector for a FNIII7-10-fused human laminin γ1 E8 fragment.

```
(xiii) Primers for amplification of FNIII7-10-
fused human laminin γ1 E8 fragment
                          (forward, SEQ ID NO: 17)
5'-GAGGTCTATATAAGCAGAGCTCTCTGGCTAACTA-3'

(reverse, SEQ ID NO: 20)
5'-GAAAGGACAGTGGGAGTGGCACC-3'
```

(3) Expression and Purification of Plus#1 Laminin E8 and Plus#2 Laminin E8

For expression of Plus#1 laminin E8 and Plus#2 laminin E8, the constructed expression vectors for the respective constituent chains were transfected into FreeStyle293-F cells (trade name, Invitrogen; hereinafter referred to as "293-F cells"). That is, in the case of Plus#1 laminin E8, the expression vector for the human laminin α1 chain LG45-fused human laminin α5 chain E8 fragment, the expression vector for the human β1 chain E8 fragment, and the expression vector for the human γ1 chain E8 fragment were transfected into 293-F cells; and in the case of Plus#2 laminin E8, the expression vector for the human α5 chain E8 fragment, the expression vector for the human β1 chain E8 fragment, and the expression vector for the FNIII7-10-fused human laminin γ1 E8 fragment were transfected into 293-F cells. In each case, 150 μg each of the three expression vectors were co-transfected into 300 ml of 293F cells ($1.0 \times 10^6$ cells/ml) with transfection reagents 293fectin (trade name, Invitrogen) and Opti-MEM (trade name, Invitrogen), the cells were cultured for 72 hours, and then the culture medium was collected. The collected culture medium was centrifuged at 1,000×g for 10 minutes, and the supernatant was further centrifuged at 15,000×g for 30 minutes for removal of remaining cells and insoluble matter. To the supernatant, 10 ml of Ni-NTA agarose (QIAGEN) was added and the protein of interest was allowed to bind thereto by overnight incubation. The Ni-NTA agarose was collected and washed successively with TBS(−) (tris-buffered saline without Ca or Mg) and 10 mM imidazole/TBS (−), and elution was performed with 200 mM imidazole/TBS(−). The protein amount in each eluted fraction was determined by measurement of the absorbance at 280 nm (A280). To the eluted fraction containing the protein of interest, 3 ml of ANTI-FLAG M2 affinity gel (Sigma) was added and the mixture was rotated at 4° C. overnight. The affinity gel was transferred into a Poly-Prep Column (Bio-Rad, #731-1550B04), which was then washed with TBS(−). Then, elution was performed with TBS(−) supplemented with 100 μg/ml FLAG peptide (Sigma, #F3290). After the eluted fractions were subjected to silver staining, the fractions of interest were combined and dialyzed against PBS(−) (phosphate-buffered physiological saline). The dialyzed product was sterilized by filtration through a 0.22-μm disk syringe filter (Millipore, #SLGV033RS) and the filtrate was stored at −80° C.

(4) SDS-PAGE Analysis of Plus#1 Laminin E8 and Plus#2 Laminin E8

The electrophoretic patterns of the purified Plus#1 laminin E8 and Plus#2 laminin E8 were compared with that of rhLM511E8 in SDS-PAGE. To a 5 to 20% gradient polyacrylamide gel (ATTO, #2331830), 1.5 μg/well of rhLM511E8, 1.9 μg/well of Plus#1 laminin E8, and 1.9 μg/well of Plus#2 laminin E8 were applied, and this was subjected to electrophoresis at 20 mA for 75 minutes. The electrophoresis was performed under reducing conditions using a buffer solution of 25 mM tris, 192 mM glycine and 0.1% sodium dodecyl sulfate according to the Laemmli method. For protein staining, Quick-CBB (WAKO, #299-50101) was used.

(5) Results

The results are shown in FIG. 1. In the lane of Plus#1 laminin E8, three bands (from the high molecular weight side, α5E8+α1LG45, γ1E8 and β1E8) were observed. The band of α5E8+α1LG45 migrated to a higher molecular weight position as compared with the band of α5E8. This result shows that α1LG45 is fused with α5E8. Similarly, in the lane of Plus#2 laminin E8, three bands (from the high molecular weight side, α5E8, γ1E8+FNIII7-10 and β1E8) were observed. The band of γ1E8+FNIII7-10 migrated to a higher molecular weight position as compared with the band of γ1E8. This result shows that FNIII7-10 is fused with γ1E8. From the above results, it was confirmed that Plus#1 laminin E8 and Plus#2 laminin E8 were obtained as designed.

Example 2

Comparison of Coating Concentration-Dependent Adhesion Efficiencies of Human iPS Cells on Various Extracellular Matrices (1) Human iPS Cells The human iPS cells used were a cell line (clone name: tic (JCRB1331)) purchased from Japanese Collection of Research Bioresources, the National Institute of Biomedical Innovation. The tic cells were maintained on mouse feeder cells according to the method recommended by Japanese Collection of Research Bioresources, the National Institute of Biomedical Innovation. To the co-culture dish, 1 U/ml dispase/DMEM-F12 was added and tic cell colonies were harvested with a scraper. The solution containing the tic cell colonies and the mouse feeder cells was filtered through a BD Falcon 100-μm cell strainer, and the cell strainer was washed. As a result, the tic cell colonies were separated. The colonies remaining in the cell strainer were collected in a xeno-free culture medium TeSR2 (trade name, STEMCELL TECHNOLOGIES), split into smaller colonies with the use of a Pipetman P-1000, resuspended in TeSR2 and seeded on a Matrigel-coated culture substrate. Expansion culture was performed at 37° C. in a 5% $CO_2$ atmosphere for 4 to 5 days. During the expansion culture, the culture medium was replaced daily. After the expansion culture, the cells were used in the experiments.

(2) Extracellular Matrices

The extracellular matrices used were Plus#1 laminin E8, Plus#2 laminin E8, and BD Matrigel for human ES cells (trade name, BD Bioscience, #354277; hereinafter referred to as "Matrigel"). For coating with these extracellular matrices, a Plus#1 laminin E8 solution, a Plus#2 laminin E8 solution and a Matrigel solution were separately diluted with phosphate-buffered physiological saline (Invitrogen, #10010-023) and added to separate BD FALCON MICROTEST 96-well microtiter plates (trade name, BD Biosciences, #353072), and the plates were allowed to stand at 4° C. overnight. The coating concentration ranges were 0.1 to 30 μg/$cm^2$ for the Matrigel solution, and 0.0038 to 3.8 μg/$cm^2$ for the Plus#1 laminin E8 solution and the Plus#2 laminin E8 solution.

(3) Measurement of Attached Cells

From the culture system in which the human iPS cells (tic cells) had been cultured in TeSR2, the culture medium was removed, a phosphate-buffered physiological saline supplemented with 4.8 mM EDTA was added, and incubation was performed at 37° C. for 3 minutes. Subsequently, the human iPS cells were incubated with TrypLE Select (trade name, Invitrogen, #12563-011) at 37° C. for 3 minutes and dissociated into single cells. After the cell number was counted, the cells were seeded at a density of $2.7 \times 10^4$ cells/well ($8.2 \times 10^4$ cells/$cm^2$) on the plates. At 6 hours after seeding, the supernatants were removed, the wells were washed with DMEM-F12 once, and the cells were fixed with a phosphate-buffered physiological saline supplemented with 10% neutral formalin for minutes. For cell staining, Diff-Quick (registered trademark, Sysmex Corporation, #16920) was used. After air-drying, the cells were lysed with 1% SDS and the absorbance at a wavelength of 595 nm was measured with a multiplate reader.

(4) Results

The results are shown in FIG. 2. The numbers of cells attached onto the Plus#1 laminin E8-coated plate and onto the Plus#2 laminin E8-coated plate were remarkably larger even at a low coating concentration (0.13 μg/$cm^2$). Meanwhile, the number of cells attached onto the plate coated with a widely used commercial product Matrigel reached the maximum at a coating concentration of 10 μg/$cm^2$. However, the maximum cell number was smaller than that in the case of Plus#1 laminin E8 and also smaller than that in the case of Plus#2 laminin E8. These results demonstrate that both Plus#1 laminin E8 and Plus#2 laminin E8 which are about 80 times less than Matrigel in terms of protein amount are more highly active for human iPS cell adhesion than Matrigel. In addition, the optimum coating concentrations of Plus#1 laminin E8 and Plus#2 laminin E8 were estimated to be about 0.13 to 3.8 μg/$cm^2$.

Example 3

Passage Culture of Human iPS Cells on Culture Substrates Coated with Various Extracellular Matrices (I)

(1) Human iPS Cells

The human iPS cells used were 32R1 cells (Masato Nakagawa, Nanako Takizawa, Megumi Narita, Tomoko Ichisaka, Shinya Yamanaka, "Promotion of direct reprogramming by transformation-deficient Myc.", Proceedings of the National Academy of Sciences, 107 (32), 14152-14157, 2010). The 32R1 cells were maintained on MSTO mouse feeder cells (Kazutoshi Takahashi, Koji Tanabe, Mari Ohnuki, Megumi Narita, Tomoko Ichisaka, Kiichiro Tomoda, Shinya Yamanaka, "Induction of pluripotent stem cells from adult human fibroblasts by defined factors.", Cell, 131 (5), 861-872, 2007).

(2) Extracellular Matrices

The extracellular matrices used were Plus#1 laminin E8, Plus#2 laminin E8, and Matrigel. For coating with Plus#1 laminin E8 and Plus#2 laminin E8, a Plus#1 laminin E8 solution and a Plus#2 laminin E8 solution were separately diluted with phosphate-buffered physiological saline and added at a concentration of 0.5 μg/$cm^2$ to separate 6-well microtiter plates, and the plates were allowed to stand at 4° C. overnight or at 37° C. for 1 hour. For coating with Matrigel, a Matrigel solution was diluted with a DMEM/F12 medium and added at a concentration of 35 μg/$cm^2$ to a 6-well microtiter plate, and the plate was allowed to stand at room temperature for 1 hour.

(3) Cell Passage and Observation

The 32R1 cells cultured on feeder cells were washed with phosphate-buffered physiological saline and treated with a cell detachment reagent (CTK solution) at 37° C. for about 2 minutes and the feeder cells were removed. Then, the 32R1 cells were harvested with a cell scraper and then seeded in each well of the extracellular matrix-coated plates. The culture media were replaced every 24 hours. The state of the cells in each plate was observed and photographed on Day 5 (1st Passage). Passages were performed on Day 7 and Day 14, and the state of the cells in each plate was observed and photographed on Day 21 (3rd Passage).

(4) Results

The observation results of the human iPS cells (32R1 cells) are shown in FIG. 3. The images in the upper row (1st Passage) show the states of the cells on the 5th day after the start of the culture on the culture substrates coated with various extracellular matrices, and the images in the middle and lower rows (3rd Passage) show the states of the cells passed twice (on the 21st day after the start of the culture on the culture substrates coated with various extracellular matrices). At the 1st Passage (Day 5), the human iPS cells hardly remained on the Matrigel-coated plate, but on the Plus#1 laminin E8-coated plate and on the Plus#2 laminin E8-coated plate, the human iPS cells were alive and attached. At the 3rd Passage (Day 21), the colonies of the human iPS cells were observed on the Plus#1 laminin E8-coated plate and on the Plus#2 laminin E8-coated plate. These results demonstrate that human iPS cells can be continuously cultured on Plus#1 laminin E8-coated culture substrates and on Plus#2 laminin E8-coated culture substrates. In the comparison between Plus#1 laminin E8 and Plus#2 laminin E8, a larger number of cells were attached onto the Plus#2 laminin E8-coated plate than onto the Plus#1 laminin E8-coated plate.

Example 4

Binding Activity of Plus#2 Laminin E8 for Recombinant Human α5β1 or α6β1 Integrin (1) Experimental Method The binding activity of Plus#2 laminin E8, rhLM511E8 or fibronectin for recombinant human α5β1 or α6β1 integrin was measured. Fibronectin was used after purified with a gelatin affinity column according to the method of Sekiguchi et al. (Kiyotoshi Sekiguchi and Sen-itiroh Hakomori, "Domain structure of human plasma fibronectin. Differences and similarities between human and hamster fibronectins.", The Journal of Biological Chemistry, 258, 3967-3973, 1983). The recombinant human α5β1 integrin was prepared with the use of the expression vectors prepared by Takagi et al. (Junichi Takagi, Harold P. Erickson, and Timothy A. Springer, "C-terminal opening mimics 'inside-out' activation of integrin α5β1.", Nature structural & molecular biology, 8 (5), 412-416, 2001). This recombinant human α5β1 integrin is composed of the extracellular domains of the α5 and β1 subunits. For dimerization of the two subunits, a sequence mainly consisting of acidic amino acid residues and hydrophobic amino acid residues is attached to the C-terminal region of the CO subunit, and a sequence mainly consisting of basic amino acid residues and hydrophobic amino acid residues is attached to the C-terminal region of the β1 subunit. Further, a FLAG tag is attached to the C-terminal region of the CO subunit, and a 6×His tag is attached to the C-terminal region of the β1 subunit. The recombinant human α6β1 integrin was prepared according to the method of Ido et al. (Hiroyuki Ido, Kenji Harada, Yoshiko Yagi, Kiyotoshi Sekiguchi, "Probing the integrin-binding site within the globular domain of laminin-511 with the function-blocking monoclonal antibody 4C7.", Matrix Biology, 25 (2), 112-117, 2006). The molecular structure of the recombinant human α6β1 integrin is the same as that of the recombinant human α5β1 integrin.

For plate coating, a Plus#2 laminin E8 solution, a rhLM511E8 solution and a fibronectin solution were separately diluted with phosphate-buffered physiological saline (Invitrogen, #10010-023) and added to separate BD FALCON MICROTEST 96-well microtiter plates (trade name, BD Biosciences, #353072), and the plates were allowed to stand at 4° C. overnight. In consideration of the molar amount, the coating concentrations were 0.4 μg/cm$^2$ for the Plus#2 laminin E8 solution, 0.32 μg/cm$^2$ for the rhLM511E8 solution, and 0.59 μg/cm$^2$ for the fibronectin solution.

The wells were blocked with a tris-buffered physiological saline supplemented with 1% (w/v) bovine serum albumin and 0.02% (v/v) Tween-20, and 10 nM recombinant human α5β1 or α6β1 integrin was added and allowed to react with the extracellular matrices in the presence of 1 mM Mn$^{2+}$ at room temperature for 3 hours. The wells were washed three times with a tris-buffered physiological saline supplemented with 1 mM Mn$^{2+}$, 0.1% (w/v) bovine serum albumin and 0.02% (v/v) Tween-20 (hereinafter referred to as "1 mM Mn$^{2+}$/0.1% BSA/TBS–T$_{0.02}$"). Then, a biotinized rabbit polyclonal antibody which recognizes the dimerization domain of the recombinant integrins was added and allowed to react with the bound recombinant integrins in the presence of 1 mM Mn$^{2+}$ at room temperature for 3 hours. The wells were washed with 1 mM Mn$^{2+}$/0.1% BSA/TBS–T$_{0.02}$ three times, and an HRP-labeled streptavidin was added and allowed to react with the biotinized rabbit polyclonal antibody in the presence of 1 mM Mn$^{2+}$ at room temperature for 15 minutes. The wells were washed with 1 mM Mn$^{2+}$/0.1% BSA/TBS–T$_{0.02}$ three times, and an o-phenylene diamine/H$_2$O$_2$ solution was added to start the chromogenic reaction. The reaction was stopped by addition of 2.5 M H$_2$SO$_4$. For the quantitative analysis of color intensity, the absorbance at a wavelength of 490 nm was measured with a multiplate reader.

(2) Results

The results are shown in FIG. 4. Plus#2 laminin E8 and human fibronectin showed a comparable binding activity for the recombinant human α5β1 integrin, but rhLM511E8 showed no binding activity for the recombinant human α5β1 integrin. Meanwhile, Plus#2 laminin E8 and rhLM511E8 showed a comparable binding activity for the recombinant human α6β1 integrin, but human fibronectin showed no binding activity for the recombinant human α6β1 integrin. These results show that Plus#2 laminin E8 is a recombinant protein having binding activity for α5β1 and α6β1 integrins.

Example 5

Single-Cell-Culture for Human ES Cells on Culture Substrates Coated with Various Extracellular Matrices (1) Human ES Cells The human ES cells used were a H9 cell line purchased from National Stem Cell Bank. The feeder cells used were SNL cells whose division had been arrested by mitomycin-C treatment (McMahon, A. P. & Bradley, A. Cell 62, 1073-1085 (1990)). On these feeder cells, the H9 cells were reseeded. The culture medium used for co-culture with the feeder cells was a culture medium for primate ES cells (ReproCELL Inc.).

(2) Extracellular Matrices

As an extracellular matrix, full-length laminin 511 was prepared according to the method described in Ido et al. (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004).

(3) Human ES Cell Culture

The H9 cells were collected from the co-culture system with SNL feeder cells as follows.

(3-1) Culture Medium Preparation

To a requisite amount of a maintenance culture medium (a mixed medium of mTeSR1 (StemCell Technologies) and NutriStem (COSMO BIO) at the ratio of 1:1), 10 mM Y-27632 was added in a 1/1000-fold amount.

(3-2) Plate Coating

To a 6-well microtiter plate, 1.5 ml/well of PBS(−) was added, 4.8 μg/well of Plus#1 laminin E8 (coating amount: 0.5 μg/cm$^2$) was added, and the plate was allowed to stand in an incubator with 5% $CO_2$ at 37° C. for 60 minutes. To the plate, 1 ml/well of a maintenance culture medium was added and allowed to be in thorough contact with the coating surface. Then, the supernatants were removed. Similarly, a 6-well microtiter plate coated with Plus#2 laminin E8 was prepared. Coating with full-length laminin 511 was also performed in a similar manner (coating amount: 2.0 μg/cm$^2$). To the coated plates, 1.5 ml/well of a maintenance culture medium (supplemented with Y-27632) was added, and the plates were stored in an incubator. For preparation of a Matrigel-coated plate, a Matrigel solution was added to a plate at coating concentrations of 0.1 to 30 μg/cm$^2$ under the same conditions as above.

(3-3) Feeder Cell Removal

The culture medium was removed, the cells were washed with 4 ml of PBS once, and the PBS was completely aspirated off. After addition of 0.5 ml of a CTK solution, incubation was performed at 37° C. When almost all of the feeder cells were detached, the CTK solution was aspirated off. The ES cells were washed with 4 ml of PBS once, 600 μl/well of ×0.5 TrypLE Select (purchased from Invitrogen) was added and allowed to be in thorough contact with the cells, and incubation was performed in an incubator with 5% $CO_2$ at 37° C. for 1 minute and successively for 3 minutes. After that, the state of the ES cells was observed with a microscope to check that the ES cells were in a round shape without intercellular adhesion. The ×0.5 TrypLE Select was removed, 3 ml/well of a maintenance culture medium was added, and the ES cells were harvested with a cell scraper.

(3-4) Cell Culture

On the coated plates (6-well plates) prepared in the above, 13,000 cells of the H9 cells which had been separated from the feeder cells and dissociated into single cells were seeded, and single-cell culture was performed in an incubator with 5% $CO_2$ at 37° C. On the following day, the supernatants were replaced with a maintenance culture medium. The culture medium was replaced every other day, and from about 6 or 7 days after the start of the culture, the culture medium was replaced daily.

(4) Results

On the culture substrates coated with various extracellular matrices, the single-cell culture of H9 cells was performed, and the colonies grown during 7-day culture were stained for alkaline phosphatase (ALP). The results are shown in FIG. 5. In FIG. 5, from the left in the upper row, a non-coated well ("None" in the figure), a Matrigel-coated well ("Matrigel" in the figure) and a full-length laminin 511-coated well ("LN511FL" in the figure) are shown; and from the left in the lower row, a Plus#1 laminin E8-coated well ("LN511E8plus#1" in the figure) and a Plus#2 laminin E8-coated well ("LN511E8plus#2" in the figure) are shown. The alkaline phosphatase staining revealed that H9 cells were favorably grown on the Plus#1 laminin E8-coated culture substrate and on the Plus#2 laminin E8-coated culture substrate as seen in the lower row of FIG. 5. Meanwhile, on the non-coated culture substrate and on the Matrigel-coated culture substrate, H9 cells were hardly observed as seen in the upper row of FIG. 5. These results show that, with the use of culture substrates coated with Plus#1 laminin E8 or Plus#2 laminin E8, a single-cell-culture method for human ES cells can easily be provided.

Example 6

Passage Culture of Human iPS Cells on Culture Substrates Coated with Various Extracellular Matrices (II)

(1) Human iPS Cells

The human iPS cells used were 32R1 cells, which had been established by transfection of four genes, i.e., the Oct3/4, KLF4, SOX2 and L-MYC genes into human adult dermal fibroblasts (aHDF-Slc7al) with the use of a retrovirus (Masato Nakagawa, Nanako Takizawa, Megumi Narita, Tomoko Ichisaka, Shinya Yamanaka, "Promotion of direct reprogramming by transformation-deficient Myc.", Proceedings of the National Academy of Sciences, 107 (32), 14152-14157, 2010).

(2) Extracellular Matrices

The extracellular matrices used were Plus#1 laminin E8, Plus#2 laminin E8, Plus#3 laminin E8 (a modified laminin in which the domains I to III of human perlecan are fused with rhLM511E8), rhLM511E8, and Matrigel. For preparation of Plus#3 laminin E8, rhLM511E8 was first prepared, and then to the N-terminal region of the human laminin β1 chain E8, the domains I to III of human perlecan (hereinafter referred to as "Pln-D1/2/3") were added. The specific procedures are as follows.

(2-1) Construction of Expression Vectors for Human Laminin α5, β1 and γ1 Chain E8 Fragments In the same manner as in the above (1-1), an expression vector for the human laminin α5 chain E8 fragment (containing the 6×His tag in the N-terminal region), an expression vector for the human laminin β1 chain E8 fragment (containing the HA tag in the N-terminal region), and an expression vector for the human laminin γ1 chain E8 fragment (containing the FLAG tag in the N-terminal region) were prepared.

(2-2) Construction of Expression Vector for Pln-D1/2/3-Fused Human Laminin β1 Chain E8 Fragment For preparation of a DNA fragment encoding a mouse Ig κ-chain V-J2-C signal peptide, Pln-D1/2/3, an HA tag and β1 chain E8 in this order from the 5' end, a DNA fragment encoding Pln-D1/2/3 was obtained and digested with a restriction enzyme HindIII. The digested product was inserted into the corresponding site of the expression vector for the human laminin β1 chain E8 fragment to give an expression vector for a Pln-D1/2/3-fused human laminin β1 chain E8 fragment.

First, PCR was performed using an expression vector for human perlecan (Shaoliang Li, Chisei Shimono, Naoko Norioka, Itsuko Nakano, Tetsuo Okubo, Yoshiko Yagi, Maria Hayashi, Yuya Sato, Hitomi Fujisaki, Shunji Hattori, Nobuo Sugiura, Koji Kimata and Kiyotoshi Sekiguchi, "Activin A Binds to Perlecan through Its Pro-region That Has Heparin/Heparan Sulfate Binding Activity", Journal of Biological Chemistry, 285 (47), 36645-36655, 2010) as a template to amplify the region corresponding to Pln-D1/2/3 ($Gly^{25}$-$Glu^{1680}$). The primers used for the PCR are as below. The primers contain a restriction enzyme HindIII recognition sequence in the 5'-terminal region. The obtained DNA fragment was digested with a restriction enzyme HindIII and inserted into the corresponding site of the expression vector for the human laminin β1 chain E8 fragment to give an expression vector for a Pln-D1/2/3-fused human laminin β1 chain E8 fragment.

```
(xiv) Primers for amplification of Pln-D1/2/3
      sequence
                              (forward, SEQ ID NO: 23)
      5'-ACGAAGCTTGGGCTGAGGGCATACGATGGC-3'

(reverse, SEQ ID NO: 24)
      5'-ATAAAGCTTCTCGACCACCAGTGGGGCTTGG-3'
```

(2-3) Expression and Purification of Plus#3 Laminin E8

Expression and purification of Plus#3 laminin E8 were performed in a similar manner as in (3) of Example 1, that is, in the same manner as in (3) of Example 1 except that the expression vector for the human α5 chain E8 fragment, the expression vector for the Pln-D1/2/3-fused human laminin β1 chain E8 fragment, and the expression vector for the human γ1 chain E8 fragment were transfected into 293-F cells.

(3) Human iPS Cell Culture

The 32R1 cells were collected from the co-culture system with SNL feeder cells as follows.

(3-1) Culture Medium Preparation

To a requisite amount of a maintenance culture medium (a mixed medium of mTeSR1 (StemCell Technologies) and NutriStem (COSMO BIO) at the ratio of 1:1), 10 mM Y-27632 was added in a 1/1000-fold amount.

(3-2) Plate Coating

To a 6-well microtiter plate, 1.5 ml/well of PBS(−) was added, 4.8 μg/well of Plus#1 laminin E8 (coating amount: 0.5 μg/cm$^2$) was added, and the plate was allowed to stand in an incubator with 5% $CO_2$ at 37° C. for 60 minutes. To the plate, 1 ml/well of a maintenance culture medium was added and allowed to be in thorough contact with the coating surface. Then, the supernatants were removed. Similarly, a 6-well microtiter plate coated with Plus#2 laminin E8 and a 6-well microtiter plate coated with Plus#3 laminin E8 were prepared (coating amount: 0.5 μg/cm$^2$ each). To the coated plates, 1.5 ml/well of a maintenance culture medium (supplemented with Y-27632) was added, and the plates were stored in an incubator. For preparation of a Matrigel-coated plate, a Matrigel solution was added to a plate at coating concentrations of 0.1 to 30 μg/cm$^2$ under the same conditions as above.

(3-3) Feeder Cell Removal

The culture medium was removed, the cells were washed with 4 ml of PBS once, and the PBS was completely aspirated off. After addition of 0.5 ml of a CTK solution, incubation was performed at 37° C. When almost all of the feeder cells were detached, the CTK solution was aspirated off. The iPS cells were washed with 4 ml of PBS once, 600 μl/well of ×0.5 TrypLE Select (purchased from Invitrogen) was added and allowed to be in thorough contact with the cells, and incubation was performed in an incubator with 5% $CO_2$ at 37° C. for 1 minute and successively for 3 minutes. After that, the state of the iPS cells was observed with a microscope to check that the iPS cells were in a round shape without intercellular adhesion. The ×0.5 TrypLE Select was removed, 3 ml/well of a maintenance culture medium was added, and the iPS cells were harvested with a cell scraper.

(3-4) Cell Culture

On the coated plates (6-well plates) prepared in the above, 13,000 cells of the 32R1 cells which had been separated from the feeder cells and dissociated into single cells were seeded, and single-cell culture was performed in an incubator with 5% $CO_2$ at 37° C. On the following day, the supernatants were replaced with a maintenance culture medium. The culture medium was replaced every other day, and from about 6 or 7 days after the start of the culture, the culture medium was replaced daily. Passage was performed every 7 to 9 days. The state of the cells in each plate before passage on the 7th day after the start of the culture was photographed (4× objective). Thereafter, after passaged to the 10th generation, the cells were immunostained for Oct3/4, SSEA-4 and TRA-1-60, and phase contrast images and fluorescence images were photographed (10× objective for each image).

(4) Results

The state of the human iPS cells in each plate before passage on the 7th day after the start of the culture is shown in FIG. 6. In FIG. 6, from the left in the upper row, a Matrigel-coated well ("Matrigel" in the figure (coating amount: 30 μg/cm$^2$)), a rhLM511E8-coated well ("E8" in the figure) and a Plus#1 laminin E8-coated well ("E8plus#1" in the figure) are shown; and from the left in the lower row, a Plus#2 laminin E8-coated well ("E8plus#2" in the figure) and a Plus#3 laminin E8-coated well ("E8plus#3" in the figure) are shown. On all the culture substrates coated with various extracellular matrices, 32R1 cells were alive and attached.

The results of the immunostaining in the human iPS cells passaged to the 10th generation on the culture substrate coated with Plus#1 laminin E8 or Plus#2 laminin E8 are shown in FIG. 7. In FIG. 7, the images in the upper two rows represent the results in the case of using the Plus#1 laminin E8-coated culture substrate ("LN511E8plus#1" in the figure), and the images in the lower two rows represent the results in the case of using the Plus#2 laminin E8-coated culture substrate ("LN511E8plus#2" in the figure). In each case, the images in the upper row are phase contrast images (PH) and the images in the lower row are immunofluorescence images (FL). As is clear from FIG. 7, in each case, the human iPS cells were positive for Oct3/4, SSEA-4 and TRA-1-60, which are markers for undifferentiated ES and iPS cells. The results show that the human iPS cells cultured using the culture substrate coated with Plus#1 laminin E8 or Plus#2 laminin E8, even after passaged to the 10th generation, were maintained in an undifferentiated state.

Example 7

Single-Cell-Culture for Human iPS Cells on Culture Substrates Coated with Various Extracellular Matrices (1) Human iPS Cells As in Examples 3 and 6, 32R1 cells were used.

(2) Extracellular Matrices

As in Example 5, Plus#1 laminin E8, Plus#2 laminin E8, full-length laminin 511, and Matrigel were used.

(3) Human iPS Cell Culture

In the same manner as in Example 3, plates were coated. In the same manner as in Example 6, 13,000 cells of the 32R1 cells which had been separated from the feeder cells and dissociated into single cells were seeded on the coated plates (6-well plates) previously prepared, and single-cell culture was performed in an incubator with 5% $CO_2$ at 37° C. On the following day, the supernatants were replaced with a maintenance culture medium. The culture medium was replaced every other day, and from about 6 or 7 days after the start of the culture, the culture medium was replaced daily.

(4) Results

On the culture substrates coated with various extracellular matrices, the single-cell culture of 32R1 cells was performed and the colonies grown during 7-day culture were stained for alkaline phosphatase (ALP). The results are shown in FIG. 8. In FIG. 8, from the left in the upper row, a non-coated well ("None" in the figure), a Matrigel-coated well ("Matrigel" in the figure) and a full-length laminin 511-coated well ("LN511FL" in the figure) are shown; and from the left in the lower row, a Plus#1 laminin E8-coated well ("LN511E8plus#1" in the figure) and a Plus#2 laminin E8-coated well ("LN511E8plus#2" in the figure) are shown. The alkaline phosphatase staining revealed that 32R1 cells were favorably grown on the Plus#1 laminin E8-coated culture substrate and on the Plus#2 laminin E8-coated culture substrate as seen in the lower row of FIG. 8. Meanwhile, on the non-coated culture substrate and on the Matrigel-coated culture substrate, 32R1 cells were hardly observed as seen in the upper row of FIG. 8. These results show that, with the use of culture substrates coated with Plus#1 laminin E8 or Plus#2 laminin E8, a single-cell-culture method for human iPS cells can easily be provided.

Example 8

Establishment of Human iPS Cells (1) Experimental Method

In Examples 6 and 7, the established human iPS cell lines were used, but in this example, establishment of human iPS cells was attempted using a culture substrate coated with Plus#1 laminin E8 or Plus#2 laminin E8. The coating concentration was 0.5 μg/cm². Specifically, on a dish coated with Plus#1 laminin E8 or Plus#2 laminin E8, reprogramming genes were transfected into human adult dermal fibroblasts (HDF1388 cells) with the use of episomal plasmid vectors pCEB-hSK-O and pCEB-hUL-G according to the method described in U.S. provisional patent application No. 61/521,153, and the cells were cultured in a maintenance culture medium (a mixed medium of mTeSR1 (StemCell Technologies) and NutriStem (COSMO BIO) at the ratio of 1:1). Human iPS cell colonies were counted 30 days after the transfection of the reprogramming genes.

The episomal plasmid pCEB-hSK-O has an expression cassette in which a construct composed of the human SOX2 coding region linked to the human KLF4 coding region via the 2A sequence, and the human OCT3/4 coding region are placed under the control of separate CAG promoters (see FIG. 10 (I)). The episomal plasmid pCEB-hUL-G has an expression cassette in which a construct composed of the human L-MYC coding region linked to the human LIN28 coding region via the 2A sequence, and the human GLIS1 coding region are placed under the control of separate CAG promoters (see FIG. 10 (II)).

These episomal plasmids were prepared with the use of the plasmids described in Okita et al., "A more efficient method to generate integration-free human iPS cells", Nature Methods, 8 (5), 409 (2011), and WO2011/016588, or other plasmids.

(2) Results

The numbers of human iPS cell colonies (the number of established cells) on the non-coated dish, the Plus#1 laminin E8-coated dish and the Plus#2 laminin E8-coated dish in three independent experiments (Exp. 1, 2 and 3) are shown in FIG. 9. In each experiment, the left bar represents the non-coated dish, the middle bar represents the Plus#1 laminin E8-coated dish, and the right bar represents the Plus#2 laminin E8-coated dish. As is clear from FIG. 9, in every experiment, the numbers of human iPS cell colonies (the number of established cells) on the Plus#1 laminin E8-coated dish and on the Plus#2 laminin E8-coated dish were larger than that on the non-coated dish, with the exception of the Plus#1 laminin E8-coated dish of Exp. 2. These results show that culture substrates coated with Plus#1 laminin E8 or Plus#2 laminin E8 are very useful in establishment of iPS cells as well.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literatures cited in the above description are incorporated herein by reference.

The invention claimed is:

1. A modified laminin having a cell-growth regulatory molecule bound to at least one site selected from the α chain N-terminus, the α chain C-terminus, the β chain N-terminus and the γ chain N-terminus of a heterotrimeric laminin fragment,
wherein the cell-growth regulatory molecule is a growth factor binding molecule,
wherein the laminin fragment is a laminin E8 fragment and has integrin binding activity,
wherein the growth factor binding molecule is one or more kinds selected from
(a) perlecan or a fragment having a perlecan growth factor binding domain thereof,
(b) agrin or a fragment having an agrin growth factor binding domain thereof,
(c) XVIII type collagen or a fragment having a XVIII type collagen growth factor binding domain thereof,
(d) syndecan or a fragment having a syndecan growth factor binding domain thereof,
(e) glypican or a fragment having a glypican growth factor binding domain thereof, and
(f) latent TGF-β binding protein or a fragment having a latent TGF-β binding protein growth factor binding domain thereof,
wherein the modified laminin is a chimeric molecule comprising the growth factor binding molecule and the laminin E8 fragment.

2. The modified laminin according to claim 1, wherein the laminin consists of one kind of α chain selected from α1 to α5, one kind of β chain selected from β1 to β3, and one kind of γ chain selected from γ1 to γ3.

3. The modified laminin according to claim 2, wherein the laminin is laminin α5β1γ1 or laminin α3β3γ2.

4. The modified laminin according to claim 1, which is of human origin.

5. A method for culturing mammalian cells, characterized by culturing the cells in the presence of the modified human laminin according to claim 1.

6. The method according to claim 5, wherein the mammalian cells are ES cells, iPS cells or somatic stem cells.

7. The method according to claim 5, wherein no feeder cells are used.

8. A culture substrate coated with the modified human laminin according to claim 1.

9. The culture substrate according to claim 8, wherein the coating concentration of the modified human laminin is 0.03 to 25 µg/cm$^2$.

10. A modified laminin having a cell-growth regulatory molecule bound to at least one site selected from the α chain N-terminus, the α chain C-terminus, the β chain N-terminus and the γ chain N-terminus of a heterotrimeric laminin fragment,
wherein the cell-growth regulatory molecule is a growth factor binding molecule,
wherein the laminin fragment is a laminin E8 fragment and has integrin binding activity,
wherein the growth factor binding molecule is one or more kinds selected from
(a) perlecan or a fragment having a perlecan growth factor binding domain thereof,
(b) agrin or a fragment having an agrin growth factor binding domain thereof,
(c) XVIII type collagen or a fragment having a XVIII type collagen growth factor binding domain thereof,
(d) syndecan or a fragment having a syndecan growth factor binding domain thereof,
(e) glypican or a fragment having a glypican growth factor binding domain thereof, and
(f) latent TGF-β binding protein or a fragment having a latent TGF-β binding protein growth factor binding domain thereof,
wherein the modified laminin is a chimeric molecule comprising the growth factor binding molecule and the laminin E8 fragment, and wherein the chimeric molecule is a fusion protein.

* * * * *